US 6,645,981 B2
(12) United States Patent
Ledoussal et al.

(10) Patent No.: US 6,645,981 B2
(45) Date of Patent: Nov. 11, 2003

(54) ANTIMICROBIAL QUINOLONES, THEIR COMPOSITIONS AND USES

(75) Inventors: Benoit Ledoussal, Mason, OH (US); Xiufeng Eric Hu, Cincinnati, OH (US); Ji-In Kim Almstead, Holmdel, NJ (US); Jeffrey Lyle Gray, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 144 days.

(21) Appl. No.: 10/017,969

(22) Filed: Dec. 14, 2001

(65) Prior Publication Data

US 2003/0008894 A1 Jan. 9, 2003

Related U.S. Application Data

(60) Provisional application No. 60/255,634, filed on Dec. 14, 2000.

(51) Int. Cl.[7] .................... A61K 31/47; C07D 401/04
(52) U.S. Cl. ............................... 514/312; 546/156
(58) Field of Search ....................... 546/156; 514/312

(56) References Cited

U.S. PATENT DOCUMENTS

| 4,844,902 A | 7/1989 | Grohe |
| 5,072,001 A | 12/1991 | Hagen et al. |
| 5,229,396 A | 7/1993 | Brighty |
| 5,328,908 A | 7/1994 | Demuth, Jr. et al. |
| 5,412,098 A | 5/1995 | Yasuhiro et al. |
| 5,457,104 A | 10/1995 | Bartel et al. |
| 5,556,979 A | 9/1996 | Phillipps et al. |
| 5,580,872 A | 12/1996 | Chu et al. |
| 5,599,816 A | 2/1997 | Chu et al. |
| 5,726,182 A | 3/1998 | Chu et al. |

FOREIGN PATENT DOCUMENTS

| EP | 0308019 A2 | 3/1989 |
| EP | 0413455 B2 | 7/1990 |
| EP | 0572259 A1 | 1/1993 |
| EP | 0775702 A1 | 5/1997 |
| EP | 0947513 A1 | 10/1997 |
| JP | 62-255482 | 11/1987 |
| JP | 03-115277 | 5/1991 |
| JP | 05-112554 | * 5/1993 |
| JP | 09-136886 | 5/1997 |
| JP | 09002953 | 7/1997 |
| JP | D10287669 | 10/1998 |
| WO | WO 91/16894 A1 | 11/1991 |
| WO | WO 95/10519 A1 | 4/1995 |
| WO | WO 98/52939 A1 | 5/1997 |
| WO | WO 98/54169 A1 | 5/1997 |
| WO | WO 99/07696 A1 | 2/1999 |
| WO | WO 99/14214 | * 3/1999 |

OTHER PUBLICATIONS

Albrecht, "Development of Antibacterial Agents of the Nalidixic Acid Type", *Prog. In Drug Research*, 1977, p. 9–104, vol. 21.

Wolfson et al., "The Fluoroquinolones: Structures, Mechanisms of Action and Resistance, and Specta of Activity in Vitro", *Antimicorbial Agents and Chemotherapy*, 1985, p. 581–586, vol. 28, No. 4.

Klopman et al., "Computer Automated Structure Evaluation of Quinolone Antibacterial Agents", *Antimicrobial Agents and Chemotherapy*, 1987, p. 1831–1840, vol. 31, No. 11.

Wentland et al., "Quinolone Antibacterial Agents", *Annual Reports in Medicinal Chemistry*, 1986, p. 145–154, vol. 20, Chapter 15.

Cornett et al., "Quinolone Antibacterial Agents", *Annual Reports in Medicinal Chemistry*, 1986, p. 139–148, vol. 21, Chapter 14.

White et al., "Quinolones", *Annual Reports in Medicinal Chemistry*, 1987, p. 117–126, vol. 22, Chapter 12, Section III—Chemotherapeutic Agents.

Koga et al., "Structure–Activity Relationships of Antibacterial 6,7– and 7,8–Disubstituted 1–alkyl–1, 4–dihydro–4–oxoquinoline–3–carboxylic Acids.", *J. Med. Chem.*, 1980, p. 1358–1363, vol. 23.

Domagala et al., "1–Substituted 7–[3–(Ethylamino)methyl]–1–pyrrolidinyl–6,8–difuoro–4–oxo–3–quinolinecarboxylic Acids. New Quantitative Structure–Activity Relationships at $N_1$ for the Quinolone Antibacterials", *J. Med. Chem.*, 1988, p. 991–1001, vol. 31.

Rosen et al., "Asymmetric Synthesis and Properties of the Enantiomers of the Atibacterial Agent 7–(3–Amino-pyrrolidin–1–yl)–1–(2,4–difluorophenyl)–1,4–dihydro–6–fluoro–4–oxo–1,8–naphthyridine–3–carboxylic Acid Hydrochloride", *J. Med. Chem.*, 1988, p. 1586–1590, vol. 31.

Ledoussal et al., "Potent Non 6–Fluoro Substituted Quinolone Antibacterials: Synthesis and Biological Activity", *J. Med. Chem.*, 1992, p. 198–200, vol. 35.

(List continued on next page.)

*Primary Examiner*—Bernard Dentz
(74) *Attorney, Agent, or Firm*—David V. Upita; Carl J. Roof

(57) ABSTRACT

Compounds of the following formula:

(I)

are effective antimicrobial agents.

20 Claims, No Drawings

OTHER PUBLICATIONS

Donagala et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", *J. Med. Chem.*, 1993, p. 871-882, vol. 36, No. 7.

Hagen et al., "Synthesis and Antibacterial Activity of New Quinolones Containing a 7-[3-(1-Amino-1-methylethyl)-1-pyrrolidinyl] Moiety. Gram-Positive Agents with Excellent Oral Activity and Low Side-Effect Potential", *J. Med. Chem.*, 1994, p. 733-738, vol. 37, No. 6.

Cecchetti et al., "Studies on 6-Aminoquinolones: Synthesis and Antibacterial Evaluation of 6-Amino-8-methylquinolones", *J. Med. Chem.*, 1996, p. 436-445, vol. 39, No. 2.

Cecchetti et al., "Potent 6-Desfluoro-8-methylquinolones as New Lead Compounds in antibacterial Chemotherapy", *J. Med. Chem.*, 1996, p. 4952-4957, vol. 39, No. 25.

Hong et al., "Novel 5-Amino-6-Methylquinolone Antibacterials: A New Class of Non-6-Fluoroquinolones", *Bioorganic & Medicinal Chem Letts.*, 1997, p. 1875-1878, vol. 7, No. 14.

Gun et al., "Synthesis and Structure—Activity Relationships of 2-Pyridones: A Novel Series of Potent DNA Gyrase Inhibitors as Antibacterial Agents", *J. Med. Chem.*, 1996, p. 3070-3088, vol. 39.

Sanders et al., "Inducible β-Lactamases: Clinical and Epidemiologic Implications for Use of Newer Cephalosporins", *Reviews of Infectious Deiseases*, Jul.-Aug. 1988, p. 830-838, vol. 10, No. 4.

Ma et al, "Synthesis and Antimicrobial Activity of 4H-4-Oxoquinolizine Derivatives: Consequences of Structural Modification at the C-8 Position", *J. Med. Chem.*, 1999, p. 4202-4213,. vol. 42, No. 20.

* cited by examiner

ANTIMICROBIAL QUINOLONES, THEIR COMPOSITIONS AND USES

CROSS REFERENCE

This application claims priority under Title 35, United States Code 119(e) from Provisional Application Ser. No. 60/255,634, filed Dec. 14, 2000.

FIELD OF THE INVENTION

The subject invention relates to novel antimicrobial compounds, their compositions and their uses.

BACKGROUND

The chemical and medical literature describes compounds that are said to be antimicrobial, i.e., capable of destroying or suppressing the growth or reproduction of microorganisms, such as bacteria. For example, such antibacterials and other antimicrobials are described in *Antibiotics, Chemotherapeutics and Antibacterial Agents for Disease Control* (M. Grayson, editor, 1982), and E. Gale et al., *The Molecular Basis of Antibiotic Action* 2d edition (1981).

The mechanism of action of these antibacterials vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. As another example, quinolones act, at least in part, by inhibiting synthesis of DNA, thus preventing the cell from replicating.

The pharmacological characteristics of antimicrobials, and their suitability for any given clinical use, vary. For example, the classes of antimicrobials (and members within a class) may vary in 1) their relative efficacy against different types of microorganisms, 2) their susceptibility to development of microbial resistance and 3) their pharmacological characteristics, such as their bioavailability, and biodistribution. Accordingly, selection of an appropriate antibacterial (or other antimicrobial) in a given clinical situation requires analysis of many factors, including the type of organism involved, the desired method of administration, the location of the infection to be treated and other considerations. there is a continuing need for broad spectrum antimicrobials, which are effective against resistant microbes.

Some 1,4-dihydroquinolone, naphthyridine or related heterocyclic moieties are known in the art to have antimicrobial activity and are described in the following references: R. Albrecht, *Prog. Drug Research*, Vol. 21, p. 9 (1977); J. Wolfson et al., "The Fluoroquinolones: Structures, Mechanisms of Action and Resistance, and Spectra of Activity In Vitro", *Antimicrob. Agents and Chemother.*, Vol. 28, p. 581 (1985); G. Klopman et al., *Antimicrob. Agents and Chemother.*, Vol. 31, p. 1831 (1987); M. P. Wentland et al., *Ann. Rep. Med. Chem.*, Vol. 20, p. 145 (1986); J. B. Cornett et al., *Ann. Rep. Med. Chem.*, Vol. 21, p. 139 (1986); P. B. Fernandes et al., *Ann. Rep. Med. Chem.*, Vol. 22, p. 117 (1987); A. Koga, et al., "Structure-Activity Relationships of Antibacterial 6,7- and 7,8-Disubstituted 1-alkyl-1,4-dihydro-4-oxoquinoline-3-carboxylic Acids", *J. Med. Chem.*, Vol. 23, pp. 1358–1363 (1980); J. M. Domagala et al., *J. Med. Chem.*, Vol. 31, p. 991 (1988); T. Rosen et al., *J. Med. Chem.*, Vol. 31, p. 1586 (1988); T. Rosen et al., *J. Med. Chem.*, Vol. 31, p. 1598 (1988); B. Ledoussal et al., "Non 6-Fluoro Substituted Quinolone Antibacterials: Structure and Activity", *J. Med Chem.*, Vol. 35, p. 198–200 (1992); J. M. Domagala et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", *J. Med. Chem.*, Vol. 36, pp. 871–882 (1993); Hagen et al., "Synthesis and Antibacterial Activity of New Quinolones Containing a 7-[3-(1-Amino-1-methylethyl)-1-pyrrolidinyl] Moiety. Gram Positive Agents with Excellent Oral Activity and Low Side-Effect Potential", *J. Med. Chem.* Vol. 37, pp. 733–738 (1994); V. Cecchetti et al., "Studies on 6-Aminoquinolines: Synthesis and Antibacterial Evaluation of 6-Amino-8-methylquinolones", *J. Med. Chem.*, Vol. 39, pp. 436–445 (1996); V. Cecchetti et al., "Potent 6-Desfluoro-8-methylquinolones as New Lead Compounds in Antibacterial Chemotherapy", *J. Med. Chem.*, Vol. 39, pp. 4952–4957 (1996); Hong et al., "Novel 5-Amino-6-methylquinolone Antibacterials: a New Class of Non-6-fluoroquinolones", *Bioorg. of Med. Chem. Let.*, Vol. 7, pp. 1875–1878 (1997); U.S. Pat. No. 4,844,902 to Grohe on Jul. 4, 1989; U.S. Pat. No. 5,072,001 to Hagen & Suto on Dec. 10, 1991; U.S. Pat. No. 5,328,908 to Demuth & White on Jul. 12, 1994; U.S. Pat. No. 5,457,104 to Bartel et al. on Oct. 10, 1995; U.S. Pat. No. 5,556,979 to Philipps et al. on Sep. 17, 1996; European Patent Appl. 572,259 of Ube Ind. pub. Dec. 1, 1993; European Patent Appl. 775,702 of Toyama Chem. Co. pub. May 28, 1997; Japanese Patent Pub. 62/255, 482 of Kyorin Pharm. Co. pub. Mar. 1, 1995.

Examples of bacterial infections resistant to antibiotic therapy have been reported in the past; they are now a significant threat to public health in the developed world. The development of microbial resistance (perhaps as a result of the intense use of antibacterials over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterials are common. See, e.g., W. Sanders, Jr. et al., "Inducible Betalactamases: Clinical and Epidemiologic Implications for Use of Newer Cephalosporins", *Reviews of Infectious Diseases*, p. 830 (1988).

Pathogenic bacteria are known to acquire resistance via several distinct mechanisms including inactivation of the antibiotic by bacterial enzymes (e.g., b-lactamases hydrolyzing penicillin and cephalosporins); removal of the antibiotic using efflux pumps; modification of the target of the antibiotic via mutation and genetic recombination (e.g., penicillin-resistance in *Neiserria gonorrhoeae*); and acquisition of a readily transferable gene from an external source to create a resistant target (e.g., methicillin-resistance in *Staphylococcus aureus*). There are certain Gram positive pathogens, such as vancomycin-resistant *Enterococcus faecium*, which are resistant to virtually all commercially available antibiotics.

Hence existing antibacterials have limited capacity in overcoming the threat of resistance. Thus it would be advantageous to provide quinolones with useful properties that can be used against resistant microbes.

SUMMARY OF THE INVENTION

Applicants have found a novel series of quinolones and related compounds that are effective against resistant microbes, and provide significant activity advantages over the art. In particular, the invention relates to compounds having a structure according to Formula (I)

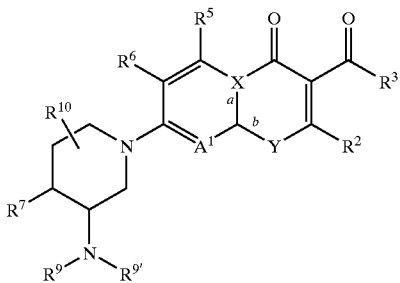

wherein:

(A)
(1) $A^1$ is selected from —N— and —$C(R^8)$—, where $R^8$ is selected from hydrogen, halo, lower alkoxy, lower alkylthio, lower alkyl, lower alkene and lower alkyne;
(2)
(a) X is selected from —C— and —N—, where (i) if X is —C—, a is a double bond and b is a single bond, and (ii) if X is —N—, a is a single bond and b is a double bond; and
(b) Y is selected from —$N(R^1)$— and —$C(R^1)$—;
(c) provided that Y is $N(R^1)$ only if X is —C— and Y is —$C(R^1)$— only if X is —N—;
(3) $R^1$ is selected from $C_3$ to about $C_6$ cycloalkyl, $C_4$ to about $C_6$ heterocycloalkyl, lower alkyl, lower alkene, a 6-membered aryl and a 6-membered heteroaryl;
(4) $R^2$ is hydrogen;
(5) $R^3$ is selected from hydrogen and hydroxy;
(6) $R^5$ is selected from hydrogen, hydroxy, amino, halo, lower alkyl, lower alkene and lower alkoxy;
(7) $R^6$ is selected from fluoro and chloro;
(8) $R^7$ is —Q—$C(R^{11})(R^{11'})(R^{11''})$, where Q is selected from —S—, —O— and —$C(R^{12})(R^{12'})$—, where $R^{12}$ and $R^{12'}$ are each independently selected from hydrogen and fluoro; where $R^{11}$, $R^{11'}$ and $R^{11''}$ are each independently selected from hydrogen, hydroxy and halo; and where $R^{11}$ and $R^{12}$ may also both be nil, such that a double bond is formed between the respective carbon atoms;
(9) $R^9$ and $R^{9'}$ are each independently selected from hydrogen and alkyl, or $R^9$ and $R^{9'}$ join to form a heterocyclic ring containing the nitrogen atom to which they are bonded; and
(10) $R^{10}$ represents the moieties on the piperidine ring other than $R^7$ and —$NR^9R^{9'}$, where each $R^{10}$ is independently selected from hydrogen, lower alkyl and fluoro; or (B) if $A^1$ is —$C(R^8)$—, X is —C— and Y is —$N(R^1)$—, then $R^8$ and $R^1$ can join to form a 6-membered heterocyclic ring, where $R^2$, $R^3$, $R^5$, $R^6$, $R^7$, $R^8$, $R^9$, $R^{9'}$ and $R^{10}$ are as described in (A): or
(C) if $A^1$ is —$C(R^8)$—, X is —C— and Y is —$N(R^1)$—, then $R^1$ and $R^2$ can join to form a monocyclic or bicyclic heterocyclic ring, where $R^3$, $R^5$, $R^6$, $R^7$, $R^8$, $R^9$, $R^{9'}$ and $R^{10}$ are as described in (A); or
(D) if $A^1$ is —$C(R^1)$—, X is —C— and Y is —$N(R^1)$—, then $R^2$ and $R^3$ can join to form a 5-membered heterocycloalkyl that is substituted with a carbonyl moiety, where $R^1$, $R^5$, $R^6$, $R^7$, $R^8$, $R^9$, $R^{9'}$ and $R^{10}$ are as described in (A);

or an optical isomer, diastereomer or enantiomer thereof; a pharmaceutically-acceptable salt, hydrate, or biohydrolyzable ester, amide or imide thereof. In addition, compounds incorporating the compounds of the invention, or using compounds of the invention as starting materials are also contemplated in this invention.

It has been found that the compounds of this invention, and compositions containing these compounds, are effective antimicrobial agents against a broad range of pathogenic microorganisms with advantages in low susceptibility to microbial resistance, reduced toxicity, and improved pharmacology.

DESCRIPTION OF THE INVENTION

I. Terms and Definitions:

The following is a list of definitions for terms used herein:

"Acyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon—carbon double bond and having 2 to 15 carbon atoms, preferably 2 to 10, more preferably 2 to 4 carbon atoms. "Alkyne" is a hydrocarbon chain having at least one (preferably only one) carbon—carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylthio" is —S—alkyl (e.g. —S—$CH_3$).

Also, as referred to herein, a "lower" alkoxy, alkylthio, alkyl, alkene or alkyne moiety (e.g., "lower alkyl") is a chain comprised of 1 to 6, preferably from 1 to 4, carbon atoms in the case of alkyl, alkoxy and alkylthio, and 2 to 6, preferably 2 to 4, carbon atoms in the case of alkene and alkyne.

"Amino" refers to a primary (—$NH_2$), secondary (—NH(alkyl), also referred to herein as "alkylamino") or tertiary (—$N(alkyl)_2$, also referred to herein as "dialkylamino").

"Aminoalkyl" is an alkyl moiety substituted with an amino, alkyl amino or dialkyl amino group (e.g., —$CH_2NH_2$, —$CH_2CH_2NH_2$, —$CH_2NHCH_3$, —$CH_2N(CH_3)_2$).

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O—aryl). Preferred aryloxy groups include (for example) phenoxy, napthyloxy, methoxyphenoxy, and methylenedioxyphenoxy.

"Carbocyclic ring" encompasses both cycloalkyl and aryl moieties, as those terms are defined herein.

"Carbonyl" is —C(=O)—.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O—alkyl or —O—heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon—carbon double bonds and/or one or more carbon—carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

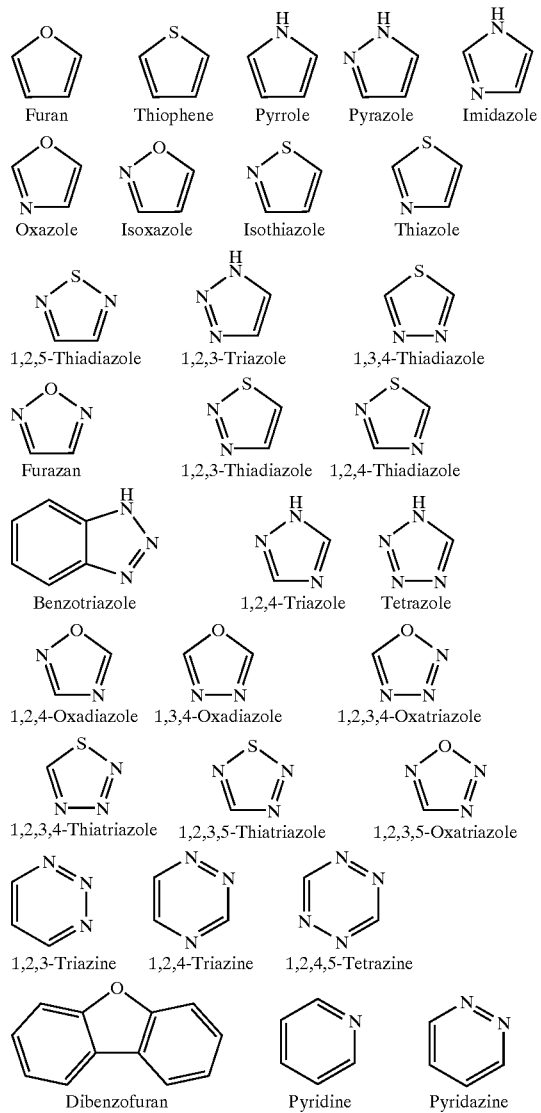

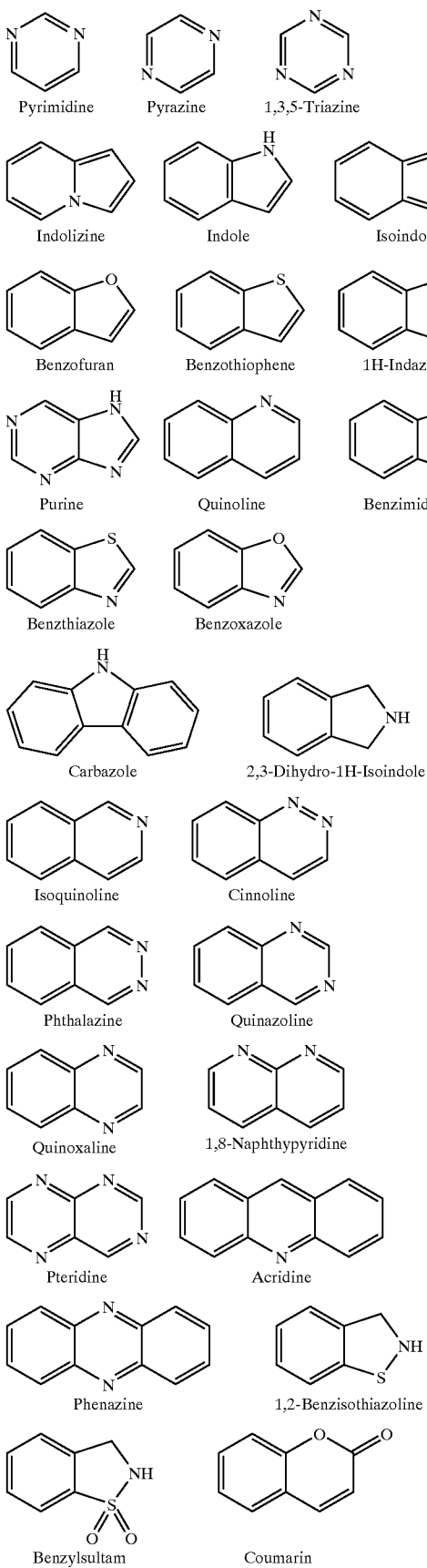
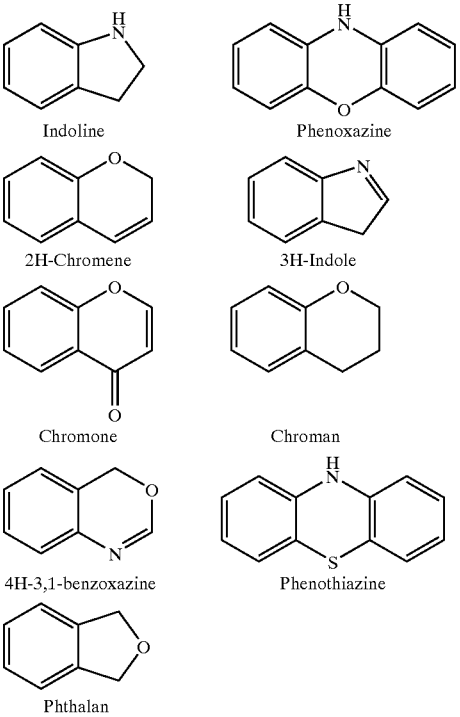

"Heteroaryloxy" is an oxygen radical having a heteroaryl substituent (i.e., —O—heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic or bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

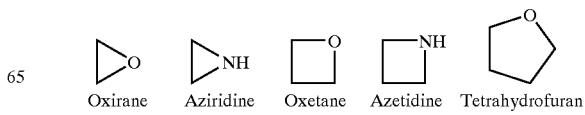

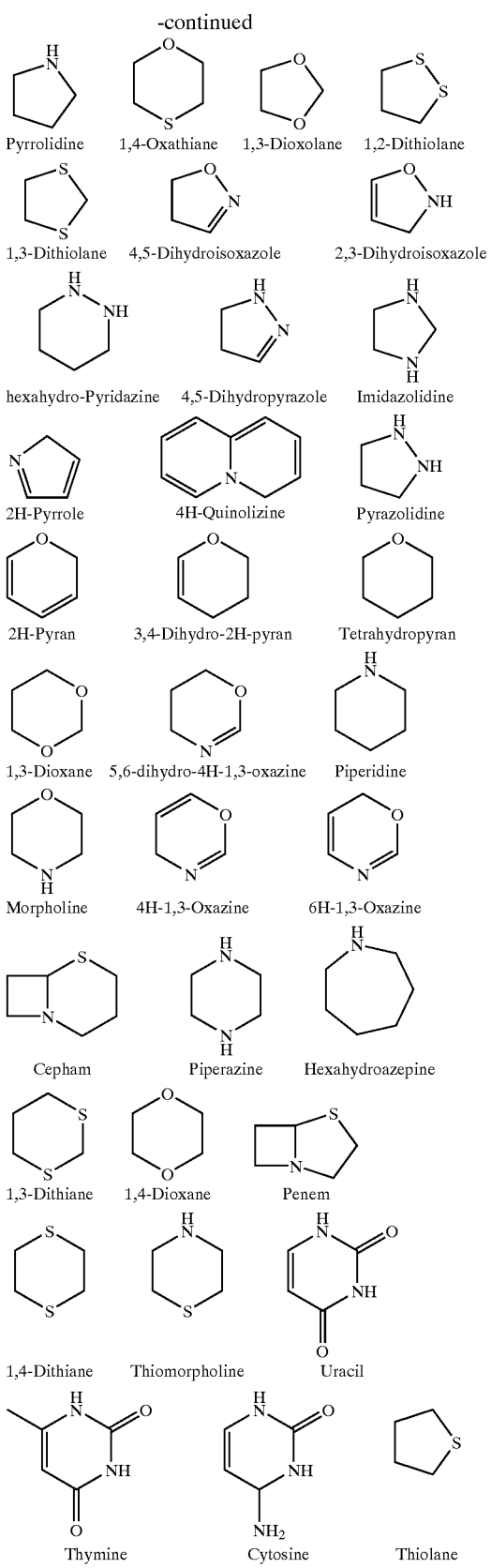

"Heterocyclic ring" encompasses both hetercycloalkyl and heteroaryl moieties, as those terms are defined herein.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

"Lower" alkoxy, alkylthio, alkyl, alkene or alkyne moiety (e.g., "lower alkyl") is a chain comprised of 1 to 6, preferably from 1 to 4, carbon atoms in the case of alkyl, alkoxy and alkylthio, and 2 to 6, preferably 2 to 4, carbon atoms in the case of alkene and alkyne.

While alkyl, heteroalkyl, cycloalkyl, and heterocycloalkyl groups may be substituted with hydroxy, amino, and amido groups as stated above, the following are not envisioned in the invention:

1. Enols (OH attached to an alkene carbon).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., carboxyl) group, or an anionic salt formed at any basic (e.g., amino, alkylamino, dialkylamino, morphylino, and the like) group on the compound of the invention. Since many of the compounds of the invention are zwitterionic, either salt is possible and acceptable. Many such salts are known in the art. Preferred cationic salts include the alkali metal salts (such as sodium and potassium), alkaline earth metal salts (such as magnesium and calcium) and organic salts, such as ammonio. Preferred anionic salts include halides, sulfonates, carboxylates, phosphates, and the like. Clearly contemplated in such salts are addition salts that may provide an optical center, where once there is none. For example, a chiral tartrate salt may be prepared from the compounds of the invention, and this definition includes such chiral salts. Salts contemplated are nontoxic in the amounts administered to the patient-animal, mammal or human.

The compounds of the invention are sufficiently basic to form acid-addition salts. The compounds are useful both in the free-base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but are not limited to hydrochloride, hydrobromide, hydroiodide, sulfate, hydrogensulfate, acetate, trifluoroacetate, nitrate, citrate, fumarate, formate, stearate, succinate, maleate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

"Host" is a substrate capable of sustaining a microbe, preferably it is a living organism, more preferably an animal, more preferably a mammal, more preferably still a human.

"Biohydrolyzable amides" are aminoacyl, acylamino, or other amides of the compounds of the invention, where the amide does not essentially interfere, preferably does not interfere, with the activity of the compound, or where the amide is readily converted in vivo by a host to yield an active compound.

"Biohydrolyzable imides" are imides of compounds of the invention, where the imide does not essentially interfere, preferably does not interfere, with the activity of the compound, or where the imide is readily converted in vivo by a host to yield an active compound. Preferred imides are hydroxyimides.

"Biohydrolyzable esters" are esters of compounds of the invention, where the ester does not essentially interfere, preferably does not interfere, with the antimicrobial activity of the compound, or where the ester is readily converted in a host to yield an active compound. Many such esters are known in the art, as described in U.S. Pat. No. 4,783,443, issued to Johnston and Mobashery on Nov. 8, 1988 (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkylacylaminoalkyl esters (such as acetamidomethyl esters).

The illustration of specific protected forms and other derivatives of the Formula 1 compounds is not intended to be limiting. The application of other useful protecting groups, salt forms, etc. is within the ability of the skilled artisan.

A "solvate" is a complex formed by the combination of a solute (e.g., a quinolone) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the quinolone or quinolone derivative (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

As used herein, a quinolone derivative includes prodrugs of a quinolone, or an active drug made from a quinolone. Preferably, such derivatives include lactams (e.g., cephems, carbacephems, penems, monolactams, etc.) covalently linked to the quinolone optionally via a spacer. Such derivatives and methods to make and use them are apparent to the skilled artisan, given the teachings of this specification.

II. Compounds:

The subject invention involves compounds of Formula (I):

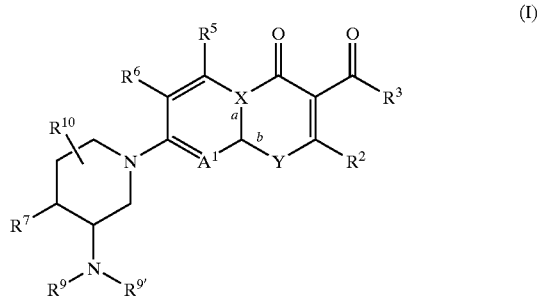

wherein $A^1$, X, Y, a, b, $R^2$, $R^3$, $R^5$, $R^6$, $R^7$, $R^8$, $R^9$, $R^{9'}$ and $R^{10}$ are as defined in the Summary of the Invention section above.

With reference to Formula (I), the description above indicates that in one embodiment (defined in sub-part (A)), the nucleus of the compounds will include only two fused rings as depicted. Alternatively, the nucleus of the compounds will include three or four fused rings, as defined in sub-parts (B) through (D). These alternative embodiments are depicted as Formula (B), Formula (C) and Formula (D), respectively, below.

With respect to each of the preferred embodiments described, a non-limiting list of preferred compounds is also set forth in tabular form. It will be recognized that for purification, administration and the like, salts and other derivatives of the above compounds are often used. Thus, a pharmaceutically-acceptable salt, hydrate, or biohydrolyzable ester, amide or imide thereof is contemplated as part of the subject invention and is meant to be included in the tables.

Table I contains a non-limiting list of preferred compounds of Formula (I) where X is a carbon atom, a represents a double bond, b represents a single bond, Y is $N(R^1)$, each $R^{10}$ is hydrogen and no additional fused rings are formed (i.e., compounds of sub-part (A)).

TABLE I

| $A^1$ | $R^1$ | $R^2$ | $R^3$ | $R^5$ | $R^6$ | $R^7$ | $R^9$ | $R^{9'}$ |
|---|---|---|---|---|---|---|---|---|
| COMe | cyclopropyl | H | OH | H | F | Et | H | H |
| CMe | cyclopropyl | H | OH | H | F | Et | H | H |
| CCl | cyclopropyl | H | OH | H | F | Et | H | H |
| CF | cyclopropyl | H | OH | H | F | Et | H | H |
| CH | cyclopropyl | H | OH | H | F | Et | H | H |
| COMe | fluorocyclopropyl | H | OH | H | F | Et | H | H |
| CMe | fluorocyclopropyl | H | OH | H | F | Et | H | H |
| CCl | fluorocyclopropyl | H | OH | H | F | Et | H | H |
| CF | fluorocyclopropyl | H | OH | H | F | Et | H | H |
| CH | fluorocyclopropyl | H | OH | H | F | Et | H | H |
| COMe | Et | H | OH | H | F | Et | H | H |
| CMe | Et | H | OH | H | F | Et | H | H |
| CCl | Et | H | OH | H | F | Et | H | H |
| CF | Et | H | OH | H | F | Et | H | H |

TABLE I-continued

| $A^1$ | $R^1$ | $R^2$ | $R^3$ | $R^5$ | $R^6$ | $R^7$ | $R^9$ | $R^{9'}$ |
|---|---|---|---|---|---|---|---|---|
| CH | Et | H | OH | H | F | Et | H | H |
| COMe | cyclopropyl | H | OH | H | F | CH(F)CH$_2$F | H | H |
| CMe | cyclopropyl | H | OH | H | F | CH(F)CH$_2$F | H | H |
| CCl | cyclopropyl | H | OH | H | F | CH(F)CH$_2$F | H | H |
| CF | cyclopropyl | H | OH | H | F | CH(F)CH$_2$F | H | H |
| CH | cyclopropyl | H | OH | H | F | CH(F)CH$_2$F | H | H |
| COMe | fluorocyclopropyl | H | OH | H | F | CH(F)CH$_2$F | H | H |
| CMe | fluorocyclopropyl | H | OH | H | F | CH(F)CH$_2$F | H | H |
| CCl | fluorocyclopropyl | H | OH | H | F | CH(F)CH$_2$F | H | H |
| CF | fluorocyclopropyl | H | OH | H | F | CH(F)CH$_2$F | H | H |
| CH | fluorocyclopropyl | H | OH | H | F | CH(F)CH$_2$F | H | H |

TABLE I-continued

| A¹ | R¹ | R² | R³ | R⁵ | R⁶ | R⁷ | R⁹ | R⁹' |
|---|---|---|---|---|---|---|---|---|
| COMe | Et | H | OH | H | F | 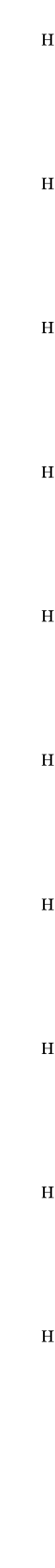 | H | H |
| CMe | Et | H | OH | H | F | 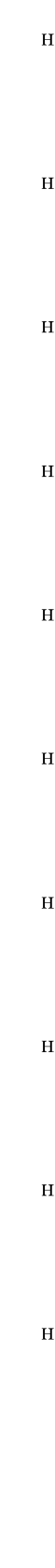 | H | H |
| CCl | Et | H | OH | H | F | 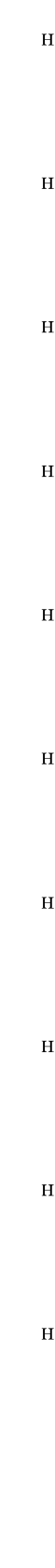 | H | H |
| CF | Et | H | OH | H | F | 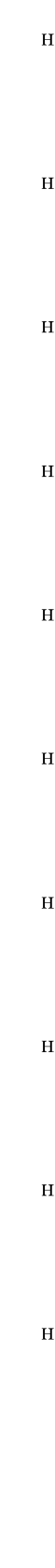 | H | H |
| CH | Et | H | OH | H | F | 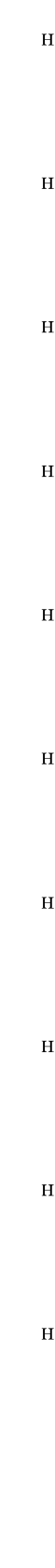 | H | H |
| COMe |  | H | OH | H | F | 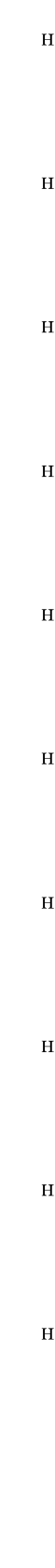 | H | H |
| CMe |  | H | OH | H | F | 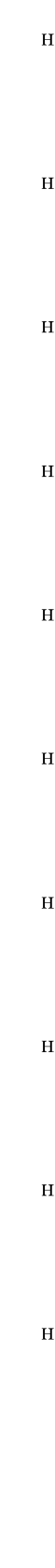 | H | H |
| CCl |  | H | OH | H | F | 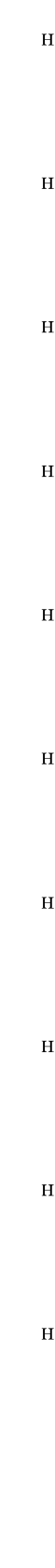 | H | H |
| CF |  | H | OH | H | F | 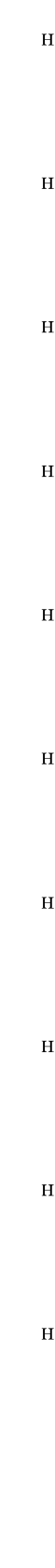 | H | H |
| CH |  | H | OH | H | F | 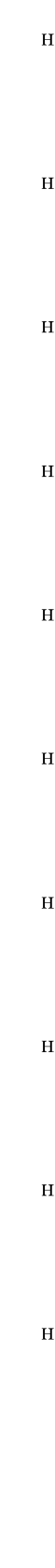 | H | H |
| COMe |  | H | OH | NH₂ | F | Et | H | H |
| CMe |  | H | OH | NH₂ | F | Et | H | H |
| CCl |  | H | OH | NH₂ | F | Et | H | H |
| CF |  | H | OH | NH₂ | F | Et | H | H |
| CH |  | H | OH | NH₂ | F | Et | H | H |
| COMe | Et | H | OH | NH₂ | F | Et | H | H |
| CMe | Et | H | OH | NH₂ | F | Et | H | H |
| CCl | Et | H | OH | NH₂ | F | Et | H | H |
| CF | Et | H | OH | NH₂ | F | Et | H | H |
| CH | Et | H | OH | NH₂ | F | Et | H | H |
| N |  | H | OH | H | F | Et | H | H |
| N |  | H | OH | NH₂ | F | Et | H | H |
| N | 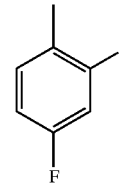 | H | OH | H | F | Et | H | H |
| N | 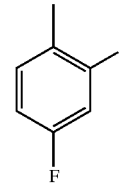 | H | OH | NH₂ | F | Et | H | H |
| N |  | H | OH | Me | F | Et | H | H |
| N | 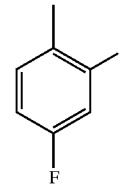 | H | OH | Me | F | Et | H | H |
| COMe |  | H | OH | H | F | Et | Me | H |

TABLE I-continued

| A¹ | R¹ | R² | R³ | R⁵ | R⁶ | R⁷ | R⁹ | R⁹' |
|---|---|---|---|---|---|---|---|---|
| CMe | cyclopropyl |  | H | OH | H | F | Et | Me | H |
| CCl | cyclopropyl |  | H | OH | H | F | Et | Me | H |
| CF | cyclopropyl |  | H | OH | H | F | Et | Me | H |
| CH | cyclopropyl |  | H | OH | H | F | Et | Me | H |
| COMe | 2-fluorocyclopropyl |  | H | OH | H | F | Et | Me | H |
| CMe | 2-fluorocyclopropyl |  | H | OH | H | F | Et | Me | H |
| CCl | 2-fluorocyclopropyl |  | H | OH | H | F | Et | Me | H |
| CF | 2-fluorocyclopropyl |  | H | OH | H | F | Et | Me | H |
| CH | 2-fluorocyclopropyl |  | H | OH | H | F | Et | Me | H |
| COMe | Et | H | OH | H | F | Et | Me | H |
| CMe | Et | H | OH | H | F | Et | Me | H |
| CCl | Et | H | OH | H | F | Et | Me | H |
| CF | Et | H | OH | H | F | Et | Me | H |
| CH | Et | H | OH | H | F | Et | Me | H |
| COMe | cyclopropyl | H | OH | NH₂ | F | Et | Me | H |
| CMe | cyclopropyl | H | OH | NH₂ | F | Et | Me | H |
| CCl | cyclopropyl | H | OH | NH₂ | F | Et | Me | H |
| CF | cyclopropyl | H | OH | NH₂ | F | Et | Me | H |
| CH | cyclopropyl | H | OH | NH₂ | F | Et | Me | H |
| COMe | Et | H | OH | NH₂ | F | Et | Me | H |
| CMe | Et | H | OH | NH₂ | F | Et | Me | H |
| CCl | Et | H | OH | NH₂ | F | Et | Me | H |
| CF | Et | H | OH | NH₂ | F | Et | Me | H |
| CH | Et | H | OH | NH₂ | F | Et | Me | H |
| N | cyclopropyl | H | OH | H | F | Et | Me | H |
| N | cyclopropyl | H | OH | NH₂ | F | Et | Me | H |
| N | 2,4-difluorophenyl | H | OH | H | F | Et | Me | H |
| N | 2,4-difluorophenyl | H | OH | NH₂ | F | Et | Me | H |
| N | cyclopropyl | H | OH | Me | F | Et | Me | H |
| N | 2,4-difluorophenyl | H | OH | Me | F | Et | Me | H |
| COMe | cyclopropyl | H | OH | H | Cl | Et | H | H |
| CMe | cyclopropyl | H | OH | H | Cl | Et | H | H |
| CCl | cyclopropyl | H | OH | H | Cl | Et | H | H |
| CF | cyclopropyl | H | OH | H | Cl | Et | H | H |

TABLE I-continued

| A¹ | R¹ | R² | R³ | R⁵ | R⁶ | R⁷ | R⁹ | R⁹' |
|---|---|---|---|---|---|---|---|---|
| CH | cyclopropyl | H | OH | H | Cl | Et | H | H |

Table Ia contains a non-limiting list of preferred compounds of Formula (Ia).

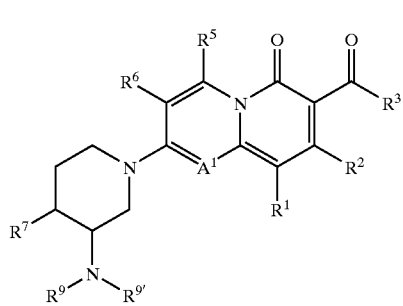

Formula (Ia)

These compounds are those of Formula (I) where X is a nitrogen atom, a represents a single bond, b represents a double bond, Y is C(R¹), each R¹⁰ is hydrogen and no additional fused rings are formed.

TABLE Ia

| A¹ | R¹ | R² | R³ | R⁵ | R⁶ | R⁷ | R⁹ | R⁹' |
|---|---|---|---|---|---|---|---|---|
| C—Me | cyclopropyl | H | OH | H | F | Et | H | H |
| C—OMe | cyclopropyl | H | OH | H | F | Et | H | H |
| C—Cl | cyclopropyl | H | OH | H | F | Et | H | H |
| C—Me | fluorocyclopropyl | H | OH | H | F | Et | H | H |
| C—OMe | fluorocyclopropyl | H | OH | H | F | Et | H | H |
| C—Cl | fluorocyclopropyl | H | OH | H | F | Et | H | H |
| C—Me | Et | H | OH | H | F | Et | H | H |
| C—OMe | Et | H | OH | H | F | Et | H | H |
| C—Cl | Et | H | OH | H | F | Et | H | H |
| C—Me | cyclopropyl | H | OH | NH₂ | F | Et | H | H |
| C—OMe | cyclopropyl | H | OH | NH₂ | F | Et | H | H |
| C—Cl | cyclopropyl | H | OH | NH₂ | F | Et | H | H |
| C—Me | fluorocyclopropyl | H | OH | NH₂ | F | Et | H | H |
| C—OMe | fluorocyclopropyl | H | OH | NH₂ | F | Et | H | H |
| C—Cl | fluorocyclopropyl | H | OH | NH₂ | F | Et | H | H |
| C—Me | cyclopropyl | H | OH | H | F | fluoropropyl | H | H |
| C—OMe | cyclopropyl | H | OH | H | F | fluoropropyl | H | H |
| C—Cl | cyclopropyl | H | OH | H | F | fluoropropyl | H | H |
| C—Me | fluorocyclopropyl | H | OH | H | F | fluoropropyl | H | H |
| C—OMe | fluorocyclopropyl | H | OH | H | F | fluoropropyl | H | H |
| C—Cl | fluorocyclopropyl | H | OH | H | F | fluoropropyl | H | H |
| C—Me | Et | H | OH | H | F | fluoropropyl | H | H |

TABLE Ia-continued

| A¹ | R¹ | R² | R³ | R⁵ | R⁶ | R⁷ | R⁹ | R⁹' |
|---|---|---|---|---|---|---|---|---|
| C—OMe | Et | H | OH | H | F |  | H | H |
| C—Cl | Et | H | OH | H | F | 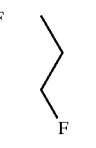 | H | H |
| C—Me |  | H | OH | H | F |  | H | H |
| C—OMe |  | H | OH | H | F |  | H | H |
| C—Cl |  | H | OH | H | F |  | H | H |
| C—Me |  | H | OH | H | F |  | H | H |
| C—OMe |  | H | OH | H | F |  | H | H |
| C—Cl |  | H | OH | H | F |  | H | H |
| C—Me | Et | H | OH | H | F |  | H | H |
| C—OMe | Et | H | OH | H | F |  | H | H |
| C—Cl | Et | H | OH | H | F |  | H | H |

TABLE Ia-continued

| A¹ | R¹ | R² | R³ | R⁵ | R⁶ | R⁷ | R⁹ | R⁹' |
|---|---|---|---|---|---|---|---|---|
| C—Me |  | H | OH | H | F | Et | Me | H |
| C—OMe |  | H | OH | H | F | Et | Me | H |
| C—Cl |  | H | OH | H | F | Et | Me | H |
| C—Me | (cyclopropyl-F) | H | OH | H | F | Et | Me | H |
| C—OMe | (cyclopropyl-F) | H | OH | H | F | Et | Me | H |
| C—Cl | (cyclopropyl-F) | H | OH | H | F | Et | Me | H |
| C—Me | Et | H | OH | H | F | Et | Me | H |
| C—OMe | Et | H | OH | H | F | Et | Me | H |
| C—Cl | Et | H | OH | H | F | Et | Me | H |

With regard to Formula (B), the compounds have a structure according to the following structure:

Formula (B)

where $R^1$ and $R^8$ of Formula (I) join to form a 6-membered heterocycloalkyl, and where D is substituted or unsubstituted —C— or —N— or D is —O— or S; $R^{13}$ and $R^{13'}$ are independently selected from hydrogen and lower alkyl; and E is selected from —O—, —S—, substituted or unsubstituted —C— and substituted or unsubstituted —N—. Preferred for D is —O—. Preferred for E is —CH₂—. Preferred is where $R^{13}$ is hydrogen and $R^{13}$ is lower alkyl, preferably methyl.

Table B contains a non-limiting list of preferred compounds of Formula (B).

TABLE B

| R² | R³ | R⁵ | R⁶ | R⁷ | R⁹ | R⁹' | Each R¹⁰ | R¹³ | R¹³' | E | D |
|---|---|---|---|---|---|---|---|---|---|---|---|
| H | OH | H | F | Et | H | H | H | Me | H | CH₂ | O |
| H | OH | H | Cl | Et | H | H | H | Me | H | CH₂ | O |
| H | OH | NH₂ | F | Et | H | H | H | Me | H | CH₂ | O |
| H | OH | Me | F | Et | H | H | H | Me | H | CH₂ | O |
| H | OH | H | F | Et | H | H | H | Me | H | CH₂ | S |
| H | OH | NH₂ | F | Et | H | H | H | Me | H | CH₂ | S |
| H | OH | Me | F | Et | H | H | H | Me | H | CH₂ | S |
| H | OH | H | F | Et | Me | H | H | Me | H | CH₂ | O |
| H | OH | NH₂ | F | Et | Me | H | H | Me | H | CH₂ | O |
| H | OH | Me | F | Et | Me | H | H | Me | H | CH₂ | O |
| H | OH | H | F | Et | Me | H | H | Me | H | CH₂ | S |
| H | OH | NH₂ | F | Et | Me | H | H | Me | H | CH₂ | S |
| H | OH | Me | F | Et | Me | H | H | Me | H | CH₂ | S |
| H | OH | H | F | -CH₂CH₂CH₂F | H | H | H | Me | H | CH₂ | O |
| H | OH | H | Cl | -CH₂CH₂CH₂F | H | H | H | Me | H | CH₂ | O |
| H | OH | NH₂ | F | -CH₂CH₂CH₂F | H | H | H | Me | H | CH₂ | O |
| H | OH | Me | F | -CH₂CH₂CH₂F | H | H | H | Me | H | CH₂ | O |
| H | OH | H | F | -CH₂CH₂CH₂F | H | H | H | Me | H | CH₂ | S |
| H | OH | NH₂ | F | -CH₂CH₂CH₂F | H | H | H | Me | H | CH₂ | S |
| H | OH | Me | F | -CH₂CH₂CH₂F | H | H | H | Me | H | CH₂ | S |
| H | OH | H | F | -CH₂CH₂CH₂F | Me | H | H | Me | H | CH₂ | O |
| H | OH | NH₂ | F | -CH₂CH₂CH₂F | Me | H | H | Me | H | CH₂ | O |

TABLE B-continued
| R² | R³ | R⁵ | R⁶ | R⁷ | R⁹ | R⁹' | Each R¹⁰ | R¹³ | R¹³' | E | D |
|---|---|---|---|---|---|---|---|---|---|---|---|
| H | OH | Me | F |  | Me | H | H | Me | H | CH₂ | O |
| H | OH | H | F |  | Me | H | H | Me | H | CH₂ | S |
| H | OH | NH₂ | F |  | Me | H | H | Me | H | CH₂ | S |
| H | OH | Me | F |  | Me | H | H | Me | H | CH₂ | S |
| H | OH | H | F |  | H | H | H | Me | H | CH₂ | O |
| H | OH | H | Cl |  | H | H | H | Me | H | CH₂ | O |
| H | OH | NH₂ | F | 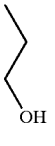 | H | H | H | Me | H | CH₂ | O |
| H | OH | Me | F | 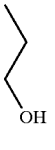 | H | H | H | Me | H | CH₂ | O |
| H | OH | H | F | 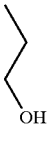 | H | H | H | Me | H | CH₂ | S |
| H | OH | NH₂ | F | 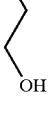 | H | H | H | Me | H | CH₂ | S |

TABLE B-continued

| R² | R³ | R⁵ | R⁶ | R⁷ | R⁹ | R⁹' | Each R¹⁰ | R¹³ | R¹³' | E | D |
|---|---|---|---|---|---|---|---|---|---|---|---|
| H | OH | Me | F |  | H | H | H | Me | H | CH₂ | S |
| H | OH | H | F |  | Me | H | H | Me | H | CH₂ | O |
| H | OH | NH₂ | F |  | Me | H | H | Me | H | CH₂ | O |
| H | OH | Me | F |  | Me | H | H | Me | H | CH₂ | O |
| H | OH | H | F |  | Me | H | H | Me | H | CH₂ | S |
| H | OH | NH₂ | F |  | Me | H | H | Me | H | CH₂ | S |
| H | OH | Me | F |  | Me | H | H | Me | H | CH₂ | S |

(Stereochemistry at the carbon atom bearing $R^{13}$ and $R^{13'}$ is preferably the S-configuration)

With regard to Formula (C), the compounds have a structure according to the following:

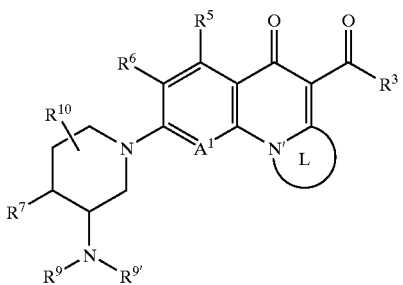

Formula (C)

where $R^1$ and $R^2$ of Formula (I) join to form ring L, which is a mono- or bicyclic heterocycle comprising N'.

Table C-1 contains a non-limiting list of preferred compounds of Formula (C) having the following formula:

TABLE C-1

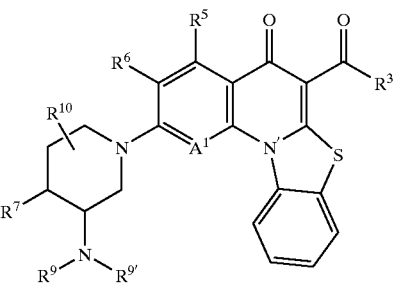

| A¹ | R³ | R⁵ | R⁶ | R⁷ | R⁹ | R⁹' | Each R¹⁰ |
|---|---|---|---|---|---|---|---|
| CH | OH | H | F | Et | H | H | H |
| CH | OH | H | Cl | Et | H | H | H |
| CF | OH | H | F | Et | H | H | H |
| N | OH | H | F | Et | H | H | H |
| CH | OH | NH₂ | F | Et | H | H | H |
| CF | OH | NH₂ | F | Et | H | H | H |

TABLE C-1-continued

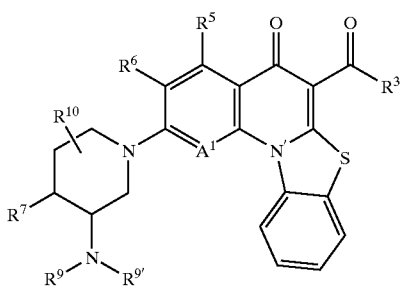

| A¹ | R³ | R⁵ | R⁶ | R⁷ | R⁹ | R⁹' | Each R¹⁰ |
|---|---|---|---|---|---|---|---|
| N | OH | NH₂ | F | Et | H | H | H |
| CH | OH | H | F | Et | Me | H | H |
| CF | OH | H | F | Et | Me | H | H |
| N | OH | H | F | Et | Me | H | H |
| CH | OH | NH₂ | F | Et | Me | H | H |
| CF | OH | NH₂ | F | Et | Me | H | H |
| N | OH | NH₂ | F | Et | Me | H | H |

Table C-2 contains a non-limiting list of preferred compounds of Formula (C) having the following formula:

TABLE C-2

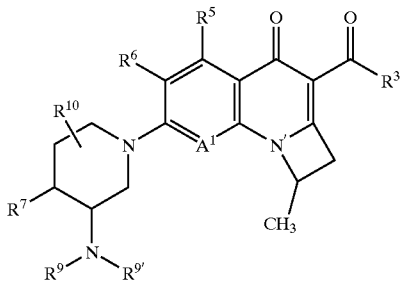

| A¹ | R³ | R⁵ | R⁶ | R⁷ | R⁹ | R⁹' | Each R¹⁰ |
|---|---|---|---|---|---|---|---|
| CH | OH | H | F | Et | H | H | H |
| CH | OH | H | Cl | Et | H | H | H |
| CF | OH | H | F | Et | H | H | H |
| N | OH | H | F | Et | H | H | H |
| CH | OH | NH₂ | F | Et | H | H | H |
| CF | OH | NH₂ | F | Et | H | H | H |
| N | OH | NH₂ | F | Et | H | H | H |
| CH | OH | H | F | Et | Me | H | H |
| CF | OH | H | F | Et | Me | H | H |
| N | OH | H | F | Et | Me | H | H |
| CH | OH | NH₂ | F | Et | Me | H | H |
| CF | OH | NH₂ | F | Et | Me | H | H |
| N | OH | NH₂ | F | Et | Me | H | H |

With regard to Formula (D), the compounds have a structure according to the following structure:

Formula (D)

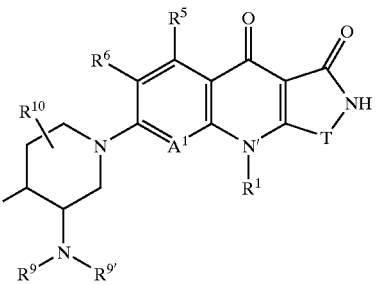

where R² and R³ of Formula (I) join to form a 5-membered heterocycloalkyl, where T is selected from —O—, —S— and substituted or unsubstituted —N—. Preferred T is —S—.

Table D contains a non-limiting list of preferred compounds of Formula (D).

TABLE D

| A¹ | R¹ | R⁵ | R⁶ | R⁷ | R⁹ | R⁹' | Each R¹⁰ | T |
|---|---|---|---|---|---|---|---|---|
| CH | cyclopropyl | H | F | Et | H | H | H | S |
| CH | cyclopropyl | H | Cl | Et | H | H | H | S |
| CF | cyclopropyl | H | F | Et | H | H | H | S |
| CH | cyclopropyl | NH₂ | F | Et | H | H | H | S |
| CF | cyclopropyl | NH₂ | F | Et | H | H | H | S |
| CH | cyclopropyl | H | F | Et | Me | H | H | S |
| CF | cyclopropyl | H | F | Et | Me | H | H | S |
| CH | cyclopropyl | NH₂ | F | Et | Me | H | H | S |
| CF | cyclopropyl | NH₂ | F | Et | Me | H | H | S |

More preferred compounds of the present invention are those where R⁸ and R¹ join to form a ring (compounds of Formula (B)) and those where none of R⁸, R¹, R² or R³ join to form a ring. Particularly preferred are those where none of R⁸, R¹, R² or R³ join to form a ring.

The following provides a description of particularly preferred moieties with respect to each of Formulas (I), (Ia), (B), (C) and (D), but is not intended to limit the scope of the claims.

$A^1$ is selected from —N— and —C($R^8$)—. Preferred is where $A^1$ is —C($R^8$)—, where $R^5$ is selected from hydrogen, halo, lower alkoxy, lower alkylthio, lower alkyl and lower alkenyl. When $R^8$ is lower alkyl, preferred is where $R^8$ has from 1 to about 2 carbon atoms; methyl is preferred. When $R^8$ is lower alkene, preferred $R^8$ will have from 2 to about 4 carbon atoms; ethenyl is preferred. When $R^8$ is lower alkoxy, preferred $R^8$ has from 1 to about 4 carbon atoms. When $R^8$ is lower alkylthio, preferred $R^8$ has from 1 to about 4 carbon atoms. All $R^8$ alkyl and alkene moieties are unsubstituted or substituted with fluoro. Preferred $R^8$ is selected from chloro, methyl, methoxy, methylthio, monofluoromethyl, difluoromethyl, trifluoromethyl, monofluoromethoxy, difluoromethoxy, and trifluoromethoxy. More preferred $R^8$ is selected from methyl substituted with from 1 to 3 fluoro, methoxy, methylthio, and chloro; especially either methoxy, methylthio or chloro.

X is selected from —C— and —N—. When X is —C—, a is a double bond and b is a single bond. In contrast, when X is —N—, a is a single bond and b is a double bond.

Y is selected from —N($R^1$)— and —C($R^1$)—. However, Y is N($R^1$) only if X is —C— and Y is —C($R^1$)— only if X is —N—.

$R^1$ is selected from $C_3$ to about $C_6$ cycloalkyl, $C_4$ to about $C_6$ heterocycloalkyl, lower alkyl, lower alkene, a 6-membered aryl and a 6-membered heteroaryl. Preferred is where $R^1$ is $C_3$ to about $C_6$ cycloalkyl, $C_3$ to about $C_6$ heterocycloalkyl, lower alkyl or lower alkene. Most preferred is $C_3$ to about $C_6$ cycloalkyl and lower alkyl. When $R^1$ is cycloalkyl, preferred are rings having from about 3 to about 5 ring carbon atoms, more preferably 3 ring carbon atoms. $R^1$ cycloalkyl moieties are preferably saturated or unsaturated with one double bond; more preferably $R^1$ cycloalkyl is saturated. When $R^1$ is linear lower alkyl, preferred is where $R^1$ contains from 1 to about 2 carbon atoms; methyl and ethyl are preferred, most preferred is ethyl. When $R^1$ is lower linear alkene, preferred is where $R^1$ contains from 2 to about 3 carbon atoms; ethenyl is preferred. When $R^1$ is branched lower alkyl or lower alkene, preferred is where $R^1$ contains from 3 to about 4 carbon atoms; branched lower alkyl is preferred; t-butyl is particularly preferred. All of the $R^1$ moieties mentioned in this paragraph are unsubstituted or substituted. When $R^1$ is substituted, preferred is one or more fluorine atoms. When $R^1$ is a 6-membered aryl or a 6-membered heteroaryl aryl, the ring is unsubstituted or substituted with from 1 to about 3 fluorine atoms, one amino group (preferably at the 3-position of the ring), one hydroxy (preferably in the 4-position of the ring), or a combination of these substituents; substituted phenyl are preferred. Most preferred $R^1$ moieties are selected from cyclopropyl, ethyl, phenyl substituted with 1 to 3 fluoro, and 4-hydroxyphenyl; more preferred is 2,4-difluorophenyl, and especially cyclopropyl or ethyl.

$R^2$ is hydrogen.

$R^3$ is selected from hydrogen and hydroxy. Preferred is hydroxy. When $R^3$ is hydroxy, it and the carbonyl to which it is attached form a carboxylic acid moiety. As such, it is a potential point of formation for the subject compounds of pharmaceutically-acceptable salts, and biohydrolizable esters, aminoacyls, and amides, as described herein. Compounds having any such variations at the $R^3$ position are included in the subject invention.

$R^5$ is selected from hydrogen, hydroxy, amino, halo, lower alkyl, lower alkene and lower alkoxy. When $R^5$ is lower alkyl, preferred is where $R^5$ has 1 to about 2 carbon atoms, preferably 1 carbon atom. When $R^5$ is lower alkene, preferred is where $R^5$ has 2 carbon atoms. When $R^5$ is lower alkoxy, preferred is where $R^5$ has from 1 to 2 carbon atoms. When $R^5$ is amino, preferred is —$NH_2$. All $R^5$ alkyl, alkene and lower alkoxy moieties are unsubstituted or substituted with fluoro moieties. Preferred $R^5$ is selected from hydrogen, hydroxy, chloro, bromo, amino, methyl, monofluoromethyl, difluoromethyl and trifluoromethyl. More preferred $R^5$ is selected from hydrogen, hydroxy, amino, and methyl; most preferred is hydrogen.

$R^6$ is selected from fluoro and chloro. Preferred is fluoro.

R is —Q—C($R^{11}$)($R^{11'}$)($R^{11''}$), where Q is selected from —S—, —O— and —C($R^{12}$)($R^{12'}$)—, where $R^{12}$ and $R^{12'}$ are each independently selected from hydrogen and fluoro; where $R^{11}$, $R^{11'}$ and $R^{11''}$ are each independently selected from hydrogen, hydroxy and halo. Alternatively, that $R^{11}$ and $R^{12}$ can both be nil, such that a double bond is formed between the respective carbon atoms. More preferred is where each of $R^{11}$, $R^{11'}$ and $R^{11''}$ is hydrogen. Also preferred is where $R^7$ is methoxy, thiomethoxy or ethyl. Most preferred is where $R^7$ is ethyl.

$R^9$ and $R^{9'}$ are each independently selected from hydrogen and alkyl (preferably lower alkyl), or $R^9$ and $R^{9'}$ join to form a heterocyclic ring containing the nitrogen atom to which they are bonded. Preferred is where $R^9$ and $R^{9'}$ are independently selected from hydrogen and methyl. Most preferred is where both $R^9$ and $R^{9'}$ are hydrogen.

$R^{10}$ represents the moieties on the piperidine ring other than the depicted $R^7$ and —$NR^9R^{9'}$ moieties, where each $R^{10}$ is independently selected from hydrogen, lower alkyl and fluoro.

As used herein, any radical is independently selected each time it is used (e.g., $R^1$ and $R^5$ need not be the same in all occurrences in defining a given compound of this invention).

The compounds of the invention may contain chiral center(s), thus any such compound includes and contemplates each optical isomer, diastereomer or enantiomer thereof, in purified or substantially purified form, and mixtures thereof, including racemic mixtures.

The following exemplary compounds are made using the procedures described herein and variations thereof which are within the purview of the skilled artisan's practice. The examples below do not limit the invention, but rather serve to illustrate some of the embodiments of the invention.

In one aspect, the present invention is directed to compounds of Formula (I) wherein X is —C—, Y is —N($R^1$)—, a is a double bond and b is a single bond. In this aspect, preferred are compounds having a structure according to the following Formula (II):

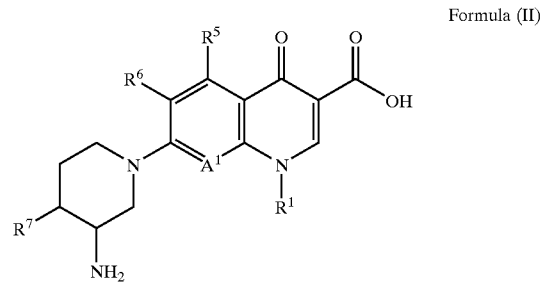

Formula (II)

where $A^1$, $R^1$, $R^5$, $R^6$ and $R^7$ are as defined with regard to Formula (I). In a particularly preferred embodiment, the compounds are those of Formula (II) where $A^1$ is —C($R^8$)—. Most preferred compounds of Formula (II) are those where $R^8$ and $R^1$ do not join to form a ring. With respect to Formula (II), most preferred is where $R^7$ is ethyl and $R^6$ is fluoro.

In another aspect, the present invention is directed to compounds of Formula (I) where X is —N—, Y is —C($R^1$)—, a is a single bond and b is a double bond. In this aspect, preferred are compounds having a structure according to the following Formula (III):

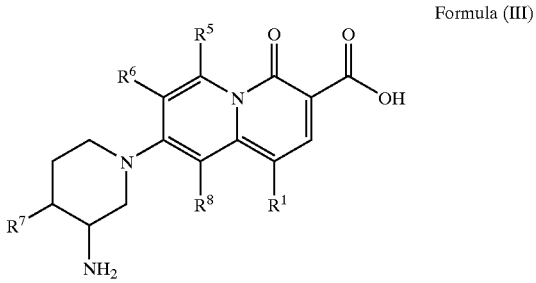

Formula (III)

where $R^1$, $R^5$, $R^6$, $R^7$ and $R^8$ are as defined with regard to Formula (I). Preferred compounds of Formula (III) are those where $R^8$ and $R^1$ do not join to form a ring. Most preferred is where $R^7$ is ethyl and $R^6$ is fluoro.

The subject invention compounds above are also useful precursors for compounds of formula Q-L-B, wherein Q is a compound of Formula 1, L is a linking moiety, and B is a lactam-containing moiety. This formula includes optical isomers, disatereomers or enantiomers thereof; pharmaceutically-acceptable salts, hydrates, or biohydrolyzable esters, amides and imides thereof. These compounds and their uses are disclosed in U.S. Pat. No. 5,180,719 issued Jan. 19, 1993; U.S. Pat. No. 5,387,748 issued Feb. 7, 1995; U.S. Pat. No. 5,491,139 issued Feb. 13, 1996; U.S. Pat. No. 5,530,116 issued Jun. 25, 1996; and European Patent Publication Nos. 366,189, published May 2, 1990, and 366,640 published May 2, 1990, all incorporated herein by reference. For compositions and methods of use, the compounds of formula Q-L-B are useful in the same way as compounds of Formula 1. Thus, they can be interchanged in the composition examples herein.

Biological activities of the invention compounds can be compared to ciprofloxacin and the other known antimicrobial quinolone compounds. Compounds of the subject invention provide better antibacterial properties against certain quinolone resistant bacteria compared to ciprofloxacin and certain other prior art compounds. When tested against quinolone-resistant bacteria such as S. aureus, S. saprophyticus, E. faecalis, S. pyogenes, S. pneumoniae, S. viridans, E. coli, P. aeruginosa, P. mirabilis, K pneumoniae, E. cloacae, certain compounds of the subject invention have been found to have MIC values (1 μg/mL) that are up to about 500 times lower than ciprofloxacin.

III. General Reaction Schemes for Compound Preparation:

In making the compounds of the invention, the order of synthetic steps may be varied to increase yield of desired product. In addition, the skilled artisan will also recognize the judicious choice of reactants, solvents, and temperatures is an important component in successful synthesis. While the determination of optimal conditions, etc. is routine, it will be understood that a variety of compounds can be generated in a similar fashion, using the guidance of the scheme below. Specific synthetic examples are set forth for a variety of compounds in Section VII.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Fieser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

General procedures for preparing quinolone moieties useful in making the compounds of the subject invention are described in the following references, all incorporated by reference herein (including articles listed within these references): *Progress in Drug Research,* Vol. 21, pp. 9–104 (1977); *J. Med. Chem.,* Vol. 23, pp. 1358–1363 (1980); *J. Med. Chem.,* Vol. 29, pp. 2363–2369 (1986); *J. Med. Chem.,* Vol. 31, p. 503 (1988); *J. Med. Chem.,* Vol. 31, pp. 503–506 (1988); *J. Med. Chem.,* Vol. 31, pp. 983–991 (1988); *J. Med. Chem.,* Vol. 31, pp. 991–1001 (1988); *J. Med. Chem.,* Vol. 31, pp. 1586–1590 (1988); *J. Med. Chem.,* Vol. 31, pp. 1598–1611 (1988); *J. Med. Chem.,* Vol. 32, pp. 537–542 (1989); *J. Med. Chem.,* Vol. 32, p. 1313 (1989); *J. Med. Chem.,* Vol. 32, pp. 1313–1318 (1989); *Drugs Exptl. Clin. Res.,* Vol. 14, pp. 379–383 (1988); *J. Pharm. Sci.,* Vol. 78, pp. 585–588 (1989); *J. Het. Chem.,* Vol. 24, pp. 181–185 (1987); *J. Het. Chem.,* Vol. 25, pp. 479–485 (1988); *Chem. Pharm. Bull.,* Vol. 35, pp. 2281–2285 (1987); *Chem. Pharm. Bull.,* Vol. 36, pp. 1223–1228 (1988); U.S. Pat. No. 4,594,347, Jun. 10, 1986; U.S. Pat. No. 4,599,334, Jul. 8, 1986; U.S. Pat. No. 4,687,770, Aug. 1, 1987; U.S. Pat. No. 4,689,325, Aug. 25, 1987; U.S. Pat. No. 4,767,762, Aug. 30, 1988; U.S. Pat. No. 4,771,055, Sep. 13, 1988; U.S. Pat. No. 4,795,751, Jan. 3, 1989; U.S. Pat. No. 4,822,801, Apr. 18, 1989; U.S. Pat. No. 4,839,355, Jun. 13, 1989; U.S. Pat. No. 4,851,418, Jul. 25, 1989; U.S. Pat. No. 4,886,810, Dec. 12, 1989; U.S. Pat. No. 4,920,120, Apr. 24, 1990; U.S. Pat. No. 4,923,879, May 8, 1990; U.S. Pat. No. 4,954,507, Sep. 4, 1990; U.S. Pat. No. 4,956,465, Sep. 11, 1990; U.S. Pat. No. 4,977,154, Dec. 11, 1990; U.S. Pat. No. 4,980,470, Dec. 25, 1990; U.S. Pat. No. 5,013,841, May 7, 1991; U.S. Pat. No. 5,045,549, Sep. 3, 1991; U.S. Pat. No. 5,290,934, Mar. 1, 1994; U.S. Pat. No. 5,328,908, Jul. 12, 1994; U.S. Pat. No. 5,430,152, Jul. 4, 1995; European Patent Publication 172,651, Feb. 26, 1986; European Patent Publication 230,053, Jul. 29, 1987; European Patent Publication 230,946, Aug. 5, 1987; European Patent Publication 247,464, Dec. 2, 1987; European Patent Publication 284,935, Oct. 5, 1988; European Patent Publication 309,789, Apr. 5, 1989; European Patent Publication 332,033, Sep. 13, 1989; European Patent Publication 342,649, Nov. 23, 1989; and Japanese Patent Publication 09/67,304 (1997).

The quinolone compounds of the subject invention may be prepared in several ways. Versatile methodologies for providing the compounds of the invention are shown in Scheme I below:

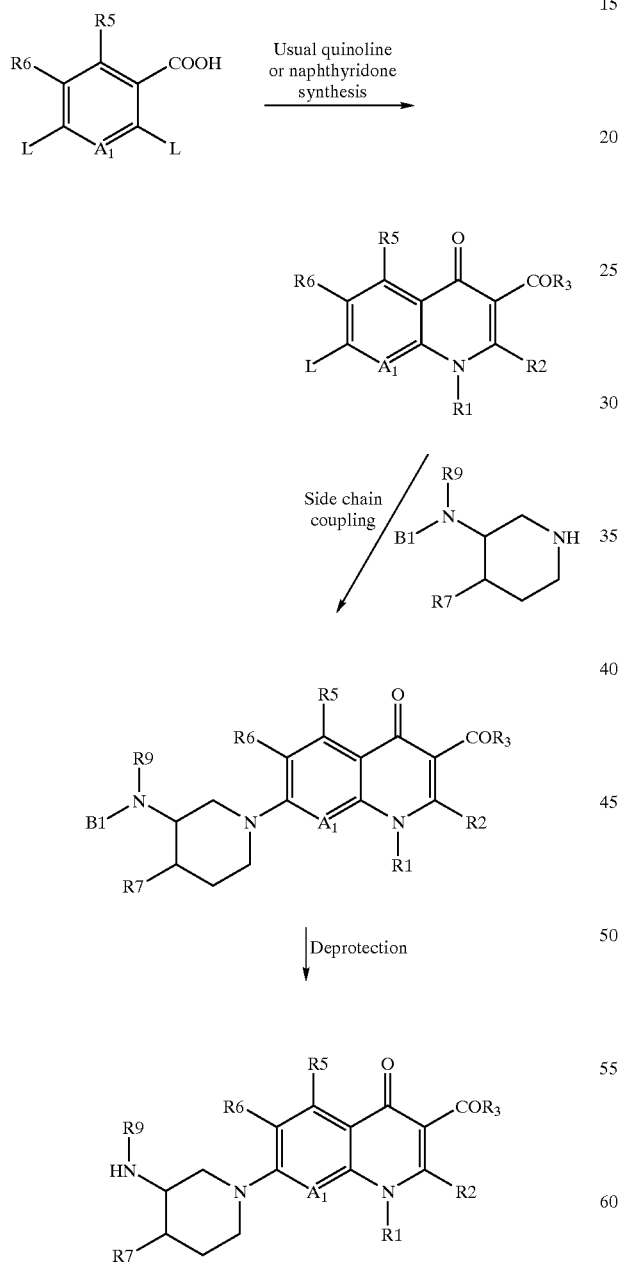

Methodologies for providing the compounds of the invention where X is —N— and Y is —C(R$^1$)— are shown in Scheme II below:

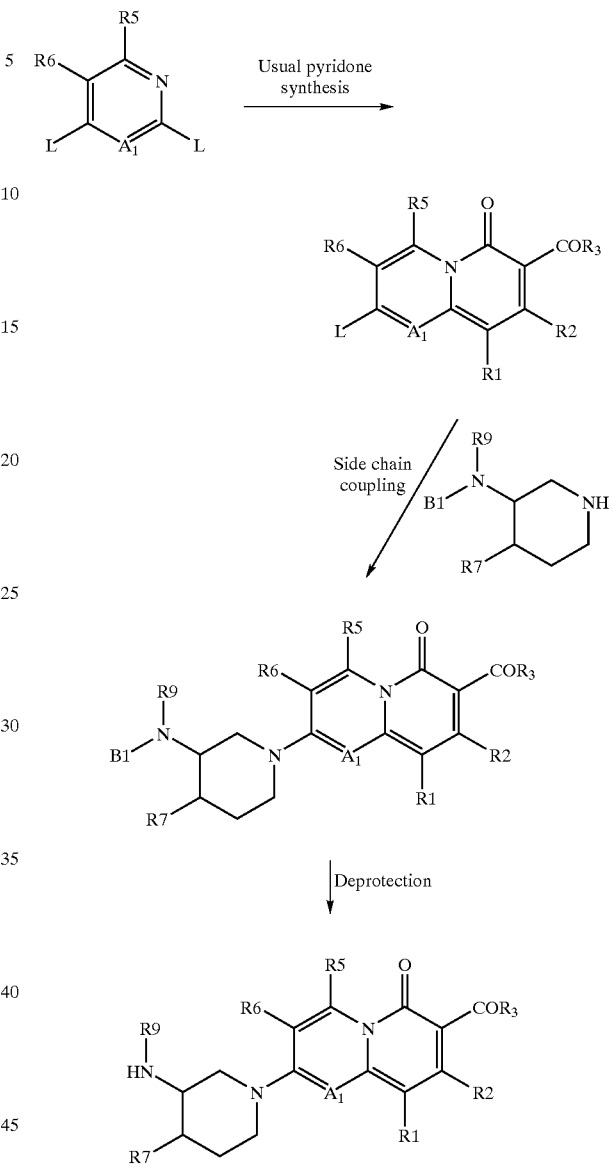

IV. Compositions:

The compositions of this invention comprise:
(a) a safe and effective amount of the compound of the invention
(b) a pharmaceutically-acceptable excipient.

The compositions may also optionally comprise other antimicrobials or other actives, which may or may not act synergistically with the invention.

A "safe and effective amount" of a quinolone is an amount that is effective, to inhibit microbial growth at the site of an infection to be treated in a host, without undue adverse side effects (such as toxicity, irritation, or allergic response), commensurate with a reasonable benefit/risk ratio when used in the manner of this invention. The specific "safe and effective amount" will vary with such factors as the particular condition being treated, the physical condition of the patient, the duration of treatment, the nature of concurrent therapy (if any), the specific dosage form to be used, the excipient employed, the solubility of the quinolone therein, and the dosage regimen desired for the composition.

The compositions of this invention are preferably provided in unit dosage form. As used herein, a "unit dosage form" is a composition of this invention containing an amount of a quinolone that is suitable for administration to a human or lower animal subject, in a single dose, according to good medical practice. These compositions preferably contain from about 30 mg, more preferably from about 50 mg, more preferably still from about 100 mg, preferably to about 20,000 mg, more preferably to about 7,000 mg, more preferably still to about 1,000 mg, most preferably to about 500 mg, of a quinolone.

The compositions of this invention may be in any of a variety of forms, suitable (for example) for oral, rectal, topical or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolone. The amount of excipient employed in conjunction with the quinolone is sufficient to provide a practical quantity of material for administration per unit dose of the quinolone. Techniques and compositions for making dosage forms useful in the methods of this invention are described in the following references, all incorporated by reference herein: *Modern Pharmaceutics*, Vol. 7, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable excipients for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight by the total composition.

In addition, dosages for injection may be prepared in dried or lyophilized form. Such forms can be reconstituted with water or saline solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH.

Various oral dosage forms can be used, including such solid forms as tablets, capsules, granules and bulk powders. These oral forms comprise a safe and effective amount, usually at least about 5%, and preferably from about 25% to about 50%, of the quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents, such are well known to the skilled artisan. Preferred excipients for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolone. Suitable excipients for topical administration preferably remain in place on the skin as a continuous film, and resist being removed by perspiration or immersion in water. Generally, the excipient is organic in nature and capable of having dispersed or dissolved therein the quinolone. The excipient may include pharmaceutically-acceptable emolients, emulsifiers, thickening agents, and solvents and the like; these are well known to the skilled artisan.

V. Methods of Using the Compounds:

This invention also provides methods of treating an infectious disorder in a human or other animal subject, by administering a safe and effective amount of a quinolone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, and antibacterial prophylaxis in post-operative patients or in immunosuppressed patients (such as patients receiving cancer chemotherapy, or organ transplant patients).

The term "treatment" is used herein to mean that, at a minimum, administration of a compound of the present invention mitigates a disease associated an infectious disorder in a host, preferably in a mammalian subject, more preferably in humans. Thus, the term "treatment" includes: preventing an infectious disorder from occurring in a host, particularly when the host is predisposed to acquiring the disease, but has not yet been diagnosed with the disease; inhibiting the infectious disorder; and/or alleviating or reversing the infectious disorder. Insofar as the methods of the present invention are directed to preventing infectious disorders, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to infectious disorders, such that administration of the compounds of the present invention may occur prior to onset of infection. The term does not imply that the disease state be completely avoided.

The quinolone derivatives and compositions of this invention can be administered topically or systemically. Systemic application includes any method of introducing the quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific quinolone used, the resistance pattern of the infecting organism to the quinolone used, the ability of the quinolone to reach minimum inhibitory concentrations at the site of the infection, the nature and extent of other infections (if any), the personal attributes of the subject (such as weight), compliance with the treatment regimen, the age and health status of the patient, and the presence and severity of any side effects of the treatment.

Typically, for a human adult (weighing approximately 70 kilograms), from about 75 mg, more preferably from about 200 mg, most preferably from about 500 mg to about 30,000 mg, more preferably to about 10,000 mg, most preferably to about 3,500 mg, of quinolone is administered per day. Treatment regimens preferably extend from about 1, preferably from about 3 to about 56 days, preferably to about 20 days, in duration. Prophylactic regimens (such as avoidance of opportunistic infections in immunocompromised patients) may extend 6 months, or longer, according to good medical practice.

A preferred method of parenteral administration is through intravenous injection. As is known and practiced in the art, all formulations for parenteral administration must be sterile. For mammals, especially humans, (assuming an approximate body weight of 70 kilograms) individual doses of from about 100 mg, preferably from about 500 mg to about 7,000 mg, more preferably to about 3,500 mg, is acceptable.

In some cases, such as generalized, systemic infections or in immune-compromised patients, the invention may be dosed intravenously. The dosage form is generally isotonic and at physiological pH. The dosage amount will depend on the patient and severity of condition, as well as other commonly considered parameters. Determination of such doses is well within the scope of practice for the skilled practitioner using the guidance given in the specification.

A preferred method of systemic administration is oral administration. Individual doses of from about 20 mg, more preferably from about 100 mg to about 2,500 mg, more preferably to about 500 mg.

Topical administration can be used to deliver the quinolone systemically, or to treat a local infection. The amounts of quinolone to be topically administered depends upon such factors as skin sensitivity, type and location of the tissue to be treated, the composition and excipient (if any) to be administered, the particular quinolone to be administered, as well as the particular disorder to be treated and the extent to which systemic (as distinguished from local) effects are desired.

VI. Examples—Compound Preparation a. Precursor Preparation—Nuclei:

Precursor Example A

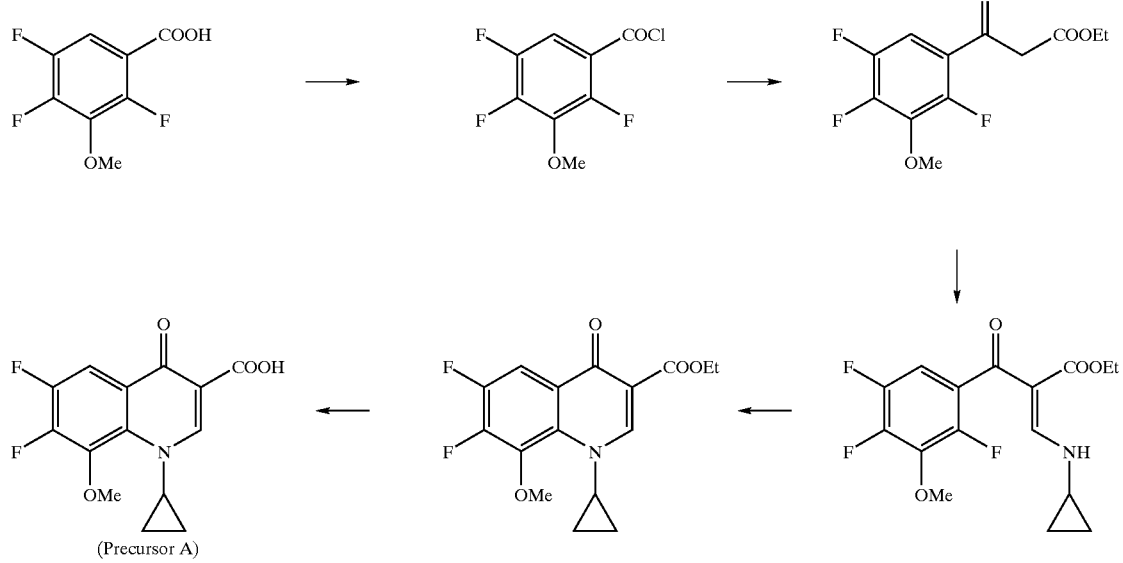

(Precursor A)

3-methoxy-2,4,5-trifluorobenzoyl chloride

3-Methoxy-2,4,5-difluorobenzoic acid (43.9 g) is suspended in dichloromethane (30 mL) and oxalyl chloride (25 mL) is added followed by 4 drops of dry dimethyl formamide (DMF). The mixture is stirred at room temperature for 6 hours and the solvent is removed by evaporation to afford the desired product.

Ethyl 2,4,5-trifluoro-3-methoxy-benzoyl acetate

Monoethyl malonate (26.4 g) is dissolved in tetrahydrofuran (THF) (700 mL). The solution is cooled at −50° C. and n-butyllithium (160 mL 2.5 M) is added, keeping the temperature below−50° C. The temperature is initially raised to 0° C. and cooled back to −50° C. 3-methoxy-2,4,5-trifluorobenzoyl chloride (20.6 g) is added, keeping the temperature at −50° C., then the reaction mixture is warmed to room temperature. Hydrochloric acid is added until the pH becomes acidic. The organic phase is washed with sodium bicarbonate and dried; evaporation of the solvent affords the desired product.

Ethyl 3-cyclopropylamino-2-(2,4,5-trifluoro-3-methoxy-benzoyl) acrylate

To a mixture of acetic anhydride (50 mL) and triethyl orthoformate (50 mL) is added ethyl 2,4,5-trifluoro-3-methoxy-benzoyl acetate (52.94 g). The mixture is refluxed for 2 hours, then is cooled to room temperature. The excess reagent is removed by evaporation to provide a thick oil which is dissolved in ethanol (150 mL). Cyclopropylamine (17.2 g) is then added while keeping the temperature at about 20° C. The desired product is isolated by filtration and air dried.

Ethyl 1-cyclopropyl-1,4-dihydro-6,7-difluoro-8-methoxy-4-oxo-quinoline-3-carboxylate Ethyl 3-cyclopropylamino-2-(2,4,5-trifluoro-3-methoxy-benzoyl) acrylate (30.3 g) is dissolved in THF. 60% sodium hydride in oil (4.1 g) is added portion-wise keeping the temperature below 40° C. The solution is stirred at room temperature for 2 hours, then poured into water. The desired product is isolated by filtration and air dried.

1-Cyclopropyl-1,4-dihydro-6,7-difluoro-8-methoxy-4-oxo-quinoline-3-carboxylic acid Ethyl-1-cyclopropyl-1,4-dihydro-6,7-difluoro-8-methoxy-4-oxo-quinoline-3-carboxylate (28.6 g) is suspended in a mixture of acetic acid, water, sulfuric acid (8/6/1, 30 mL) and is refluxed for 2 hours. The reaction mixture is cooled at 0° C. and the desired product is collected by filtration.

Precursor Example B

2,6-dichloro-5-fluoro-3-nicotinoyl chloride 2,6-dichloro-5-fluoro-3-nicotinic acid (4 g) is suspended in CH$_2$Cl$_2$ and oxalyl chloride (2.72 g) is added followed by 3 drops of DMF. The mixture is allowed to stir for 3 hours at room temperature and the solvent is evaporated to afford the desired product.

Ethyl-3-(2,6-dichloro-5-fluoropyridinyl)-3-oxo-2-carboxyethyl propanoate

Magnesium turnings (0.44 g) are added to a mixture of ethanol (1.5 mL) and carbon tetrachloride (0.15 mL) and diethyl malonate (2.76 mL) is added over 15 minutes. The temperature is maintained at 50° C. for 2 hours and then cooled at 0° C. 2,6-dichloro-5-fluoro-3-nicotinoyl chloride (4.3 g) is progressively added keeping the temperature below 5° C. After one hour at room temperature, the mixture is acidified, diluted with water and extracted with toluene. Evaporation of the solvent affords the desired product.

Ethyl-3-(2,6-dichloro-5-fluoropyridinyl)-3-oxo-propanoate

Ethyl-3-(2,6-dichloro-5-fluoropyridinyl)-3-oxo-2-carboxyethyl propanoate (6 g) is mixed with water (30 mL) and p-toluene sulfonic acid (0.15 g) and heated at 100° C. for one hour. After cooling at room temperature the desired product is extracted with ethyl acetate and the desired product is obtained by evaporation of the solvents.

Ethyl-3-(2,6-dichloro-5-fluoropyridinyl)-3-oxo-2-ethoxymethylene-propanoate

Ethyl-3-(2,6-dichloro-5-fluoropyridinyl)-3-oxo-propanoate (5 g) is mixed with triethyl orthofomate (4.3 mL)

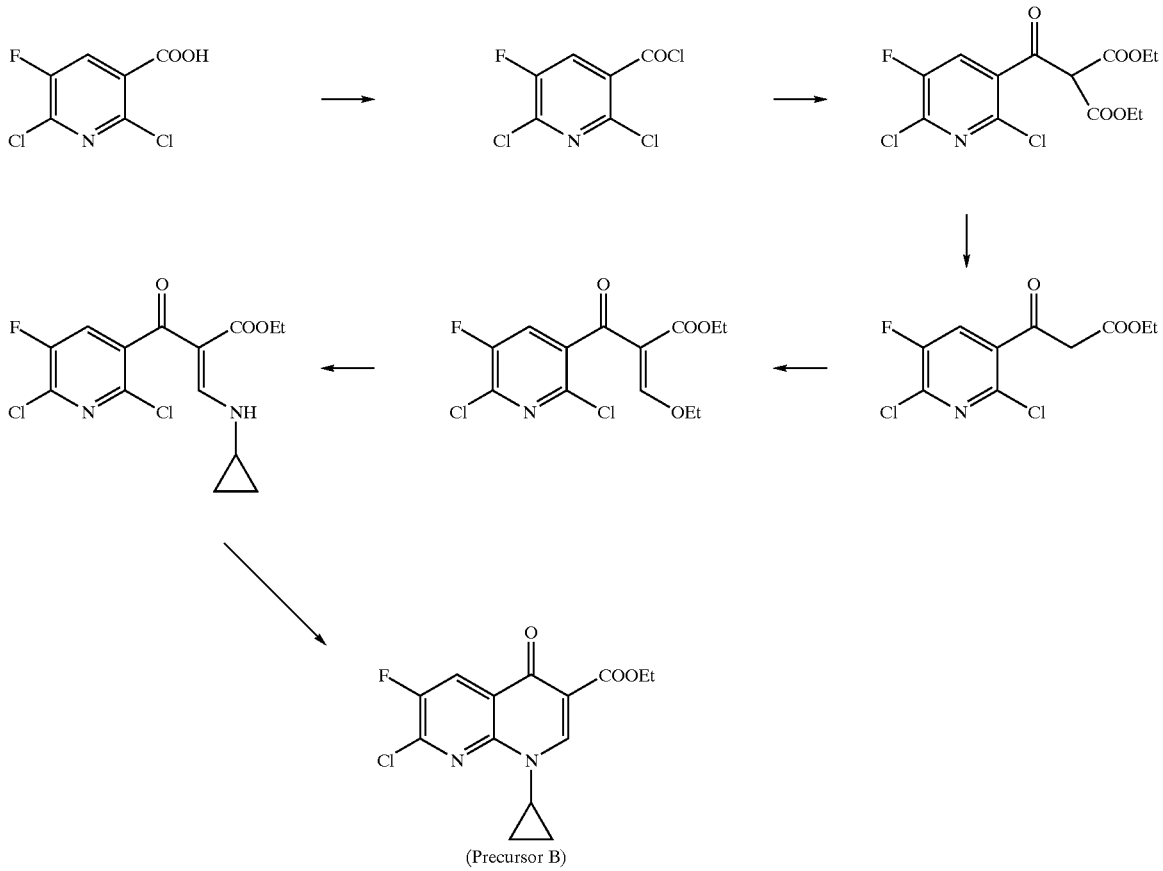

(Precursor B)

and acetic anhydride (4.1 mL) and is refluxed for 2 hours. The mixture is then concentrated under vacuum to afford the desired product.

Ethyl-3-(2,6-dichloro-5-fluoropyridinyl)-3-oxo-2-cyclopropylaminomethylene-propanoate Ethyl-3-(2,6-dichloro-5-fluoropyridinyl)-3-oxo-2-ethoxymethylene-propanoate (2.65 g) is dissolved in ethanol (5 mL) and the solution is cooled at 0° C. Cyclopropylamine (0.8 mL) is added progressively and the mixture is allowed to stir at room temperature for one hour. The desired product is obtained after evaporation of the solvent.

Ethyl-7-chloro-1-cyproplyl-6-fluoro-4-oxo-1,4-dihydro-naphthyridine-3-carboxylate Ethyl-3-(2,6-dichloro-5-fluoropyridinyl)-3-oxo-2-cyclopropylaminomethylene-propanoate (1.09 g) is dissolved in acetonitrile (15 mL) and potassium carbonate (840 mg) is added. The mixture is refluxed for 18 hours and poured on water. The precipitate is filtered and purified by chromatography using dichloromethane 98/methanol 2.

Precursor Example C and acetic anhydride (10 mL) and the solution is refluxed for 3 hours. After concentration under vacuum, the residue is dissolved in dichloromethane and cooled at 0 C. (S)-2-aminopropanol (4.26 g) is added dropwise and the solution is allowed to warm at room temperature. The product is obtained after chromatography using hexane 75, ethyl acetate 25.

(3S) ethyl-9,10-difluoro-2,3-dihydro-3-methyl-7-oxo-7H-pyridol[1.2,3-de]-1,4-benzoxazine-6-carboxylate Ethyl-3-(2,3,4,5-tetrafluorophenyl)-3-oxo-2-[(2,S)3-amino-2-methyl-propanol-3-yl]-methylene-propanoate

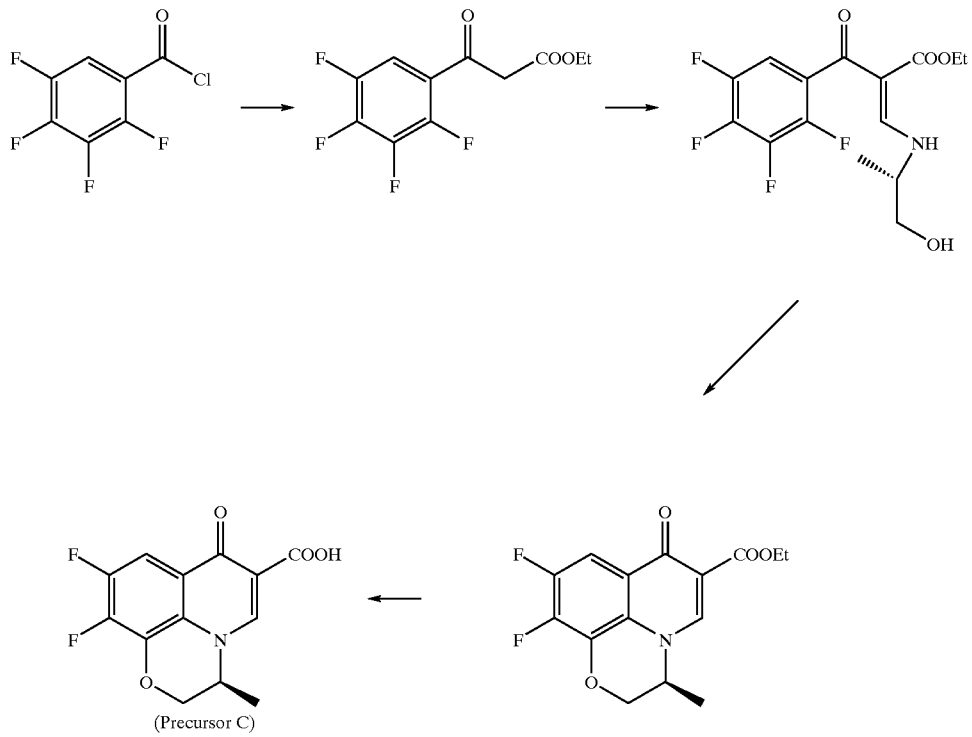

(Precursor C)

Ethyl-3-(2,3,4,5-tetrafluorophenyl)-3-oxo-propanoate

Ethyl hydrogen malonate (26.4 g) is dissolved in THF (700 mL) and the solution is cooled at −35° C. 2.5 M nBuLi (160 mL) is added dropwise and the solution is cooled at −58° C. A solution of 2,3,4,5-tetrafluorobenzoyl chloride (21.1 g) in THF (10 mL) is added and then the reaction is allowed to warm at room temperature. The solution is poured in 1N HCl and extracted with ether. The extracts are washed with a bicarbonate solution, brine and dried over Sodium sulfate. The desired product is obtained after chromatography with hexane 85, ethyl acetate 15 (24.8 g).

Ethyl-3-(2,3,4,5-tetrafluorophenyl)-3-oxo-2-[(2,S)3-amino-2-methyl-propanol-3-yl]-methylene-propanoate Ethyl-3-(2,3,4,5-tetrafluorophenyl)-3-oxo-propanoate (10 g) is dissolved in a mixture of triethyl orthoformate (10 mL)

(9.78 g) is dissolved in DMF (25 mL) and sodium hydride (1.17 g) is added. After 20 minutes at room temperature, the solution is heated overnight. The solvent is removed under vacuum and the residue is treated with water. The desired product is obtained by filtration.

(3S) 9,10-difluoro-2,3-dihydro-3-methyl-7-oxo-7H-pyrido[1,2,3-de]-1,4-benzoxazine-6-carboxylic acid (3S) ethyl-9,10-difluoro-2,3-dihydro-3-methyl-7-oxo-7H-pyrido[1,2,3-de]-1,4-benzoxazine-6-carboxylate (8.2 g) is dissolved in THF and 10% aqueous KOH (25 mL) is added. The solution is heated to 65° C. for 2 hours. The THF is evaporated and the pH is adjusted to 3 by addition of acetic acid. The desired product is obtained by filtration.

Precursor Example D

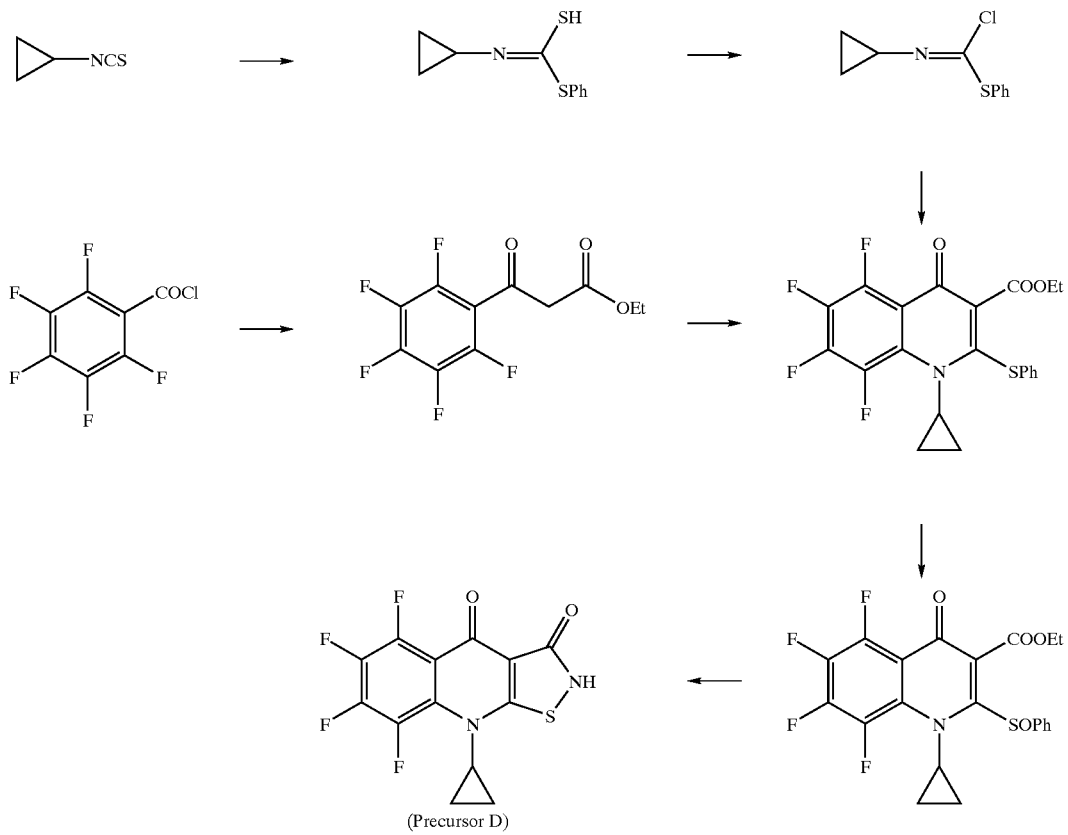

(Precursor D)

Phenyl N-cyclopropyliminomercaptothioformate

N-Cyclopropyl isothiocyanate (5 g) and thiophenol (5.2 mL) are mixed together at 0° C. After stirring 30 minutes at 0° C., two drops of triethylamine are added to initiate the reaction. The mixture immediately becomes yellow and slowly solidified. The white solid is broken apart and filtered, washing with hexanes to provide the desired product.

Phenyl N-cyclopropyliminochlorothioformate

Phosphorus pentachloride (10.5 g) is added to Phenyl N-cyclopropyliminomercaptothioformate, the flask is equipped with a reflux condenser, and the solid mixture is heated to 65° C. under argon. The solids slowly melted to become a yellow solution. The mixture is allowed to stir 6 hr at 65° C., then is cooled to room temperature. The flask is equipped with a distillation apparatus and the desired product is distilled.

2,3,4,5,6-Pentafluorobenzoylacetate

Ethyl hydrogen malonate (33.69 g) is dissolved in dry THF (640 mL). The mixture is cooled to −78° C. and n-butyllithium (319 mL, 1.6 M) is added at a rapid drop rate such that the internal temperature remains below −30° C. The cooling bath is then removed and the mixture is allowed to warm to −20° C. The reaction is re-cooled to −78° C. and 2,3,4,5,6-pentafluorobenzoyl chloride (25 g) is added in dry THF (40 mL) via cannula. The yellow solution is allowed to warm to room temperature and stir overnight. The reaction mixture is poured into a vigorously stirring solution of diluted HCl (125 mL) and allowed to stir 1 hr, before the layers are separated and the aqueous layer is extracted with ether. The organic phase is washed with saturated aqueous sodium bicarbonate solution and brine and dried over MgSO4. After concentrating, the desired product is distilled at 5 mm Hg.

Ethyl 1-cyclopropyl-2-phenylthio-5,6,7,8-tetrafluoro-1,4-dihydro-4-oxoquinoline-3-carboxylate 2,3,4,5,6-Pentafluorobenzoylacetate (6.02 g) is dissolved in dry toluene (100 mL). Dry sodium hydride (0.562 g) is added under argon and the mixture is allowed to stir 30 minutes. Phenyl N-cyclopropyliminochlorothioformate (6.78 g) is then added in dry toluene (15 mL). The resulting mixture is heated to 50° C. for 4 hr, then to reflux for 20 hr before being cooled to room temperature and diluted with dichloromethane. The organic layer is washed once with water, dried over MgSO4, and concentrated to give a dark oil which is applied to a column of silica gel with 15% acetone in hexanes.

Ethyl 1-cyclopropyl-2-phenylsulfinyl-5,6,7,8-tetrafluoro-1,4-dihydro-4-oxoquinoline-3-carboxylate Ethyl 1-cyclopropyl-2-phenylthio-5,6,7,8-tetrafluoro-1,4-dihydro-4-oxoquinoline-3-carboxylate (3.38 g) is dissolved in dichloromethane (100 mL). m-Chloroperbenzoic acid (1.9 g) is added and the solution is allowed to stir at room temperature overnight. The reaction mixture is extracted with sodium bicarbonate, dried over MgSO4 and concentrated under vacuum. The desired product is obtained after purification by chromatography, using 15% acetone in hexanes.

5,6,7,8-tetrafluoro-9-cyclopropyl-1,3,4,9-tetrahydroisothiazolo[5,4-b]quinoline-3,4-dione Ethyl 1-cyclopropyl-2-phenylsulfinyl-5,6,7,8-tetrafluoro-1,4-dihydro-4-oxoquinoline-3-carboxylate (0.225 g) is dissolved in THF (15 mL) and the solution is cooled at 0° C.

Sodium hydrosulfite (60 mg) dissolved in water (2 mL) is then added followed by a solution of sodium bicarbonate (0.5 g in 10 mL). The solution is stirred at 0° C. for one hour and hydroxylamine—O—sulfonic acid (0.264 g) is added. The solution is allowed to warm at room temperature and after 3 hours is treated with diluted hydrochloric acid. The crude desired product is collected by filtration and purified by crystallization in ethanol.

Precursor Example E

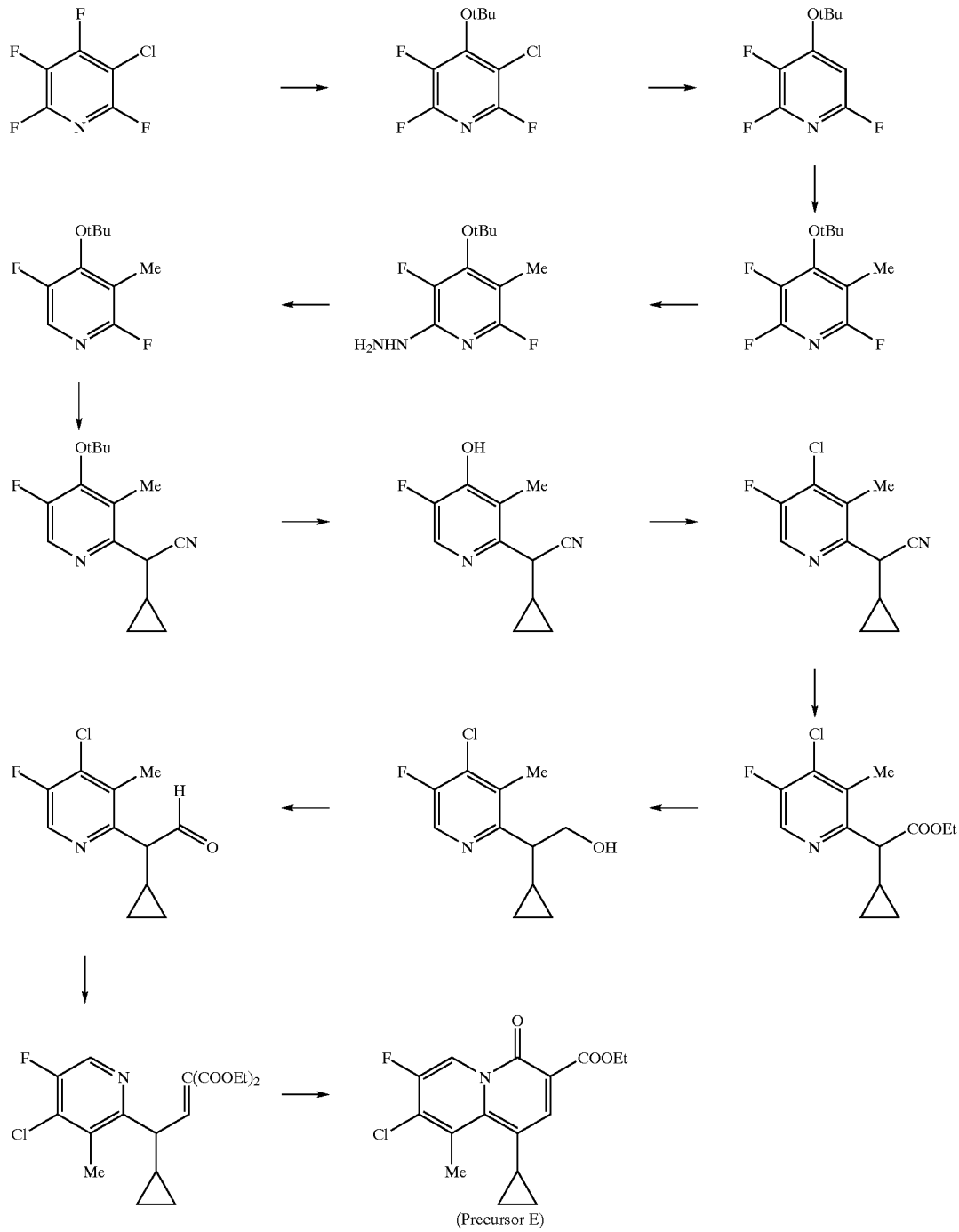

(Precursor E)

4-tert-Butoxy-3-chloro-2,5,6-trifluoropyridine

3-Chloro-2,4,5,6-tetrafluoropyridine (50.0 g) is dissolved in dry THF (500 mL) and cooled to 0° C. A solution of lithium tert-butoxide (270 mL, 1.0 M in THF) is added dropwise over 50 minutes and the solution is then allowed to stir an additional 90 min. at 0° C. before warming to room temperature. The reaction mixture is poured into hexanes (1000 mL) and filtered through a pad of Celite®. After concentration via rotary evaporation, the liquid is applied to a column of silica gel in hexanes to isolate the desired compound.

4-tert-Butoxy-2,5,6-trifluoropyridine

Sodium acetate (12.75 g) and palladium on carbon (18.66 g, 10% Pd) are added to a solution of 4-tert-butoxy-3-chloro-2,5,6-trifluoropyridine (31.028 g) in THF (800 mL) and the mixture is placed under hydrogen (1 atm). The mixture is allowed to stir at room temperature for 48 h. The palladium is removed by filtration through a pad of Celite®, which is washed with hexanes. After concentration, the liquid is applied to a column of silica gel in 5% ether in petroleum ether to isolate the desired compound.

4-tert-Butoxy-2,3,6-trifluoro-5-methylpyridine n-Butyllithium (45.6 mL, 2.5 M in hexanes) is added via syringe to a solution of dry diisopropylamine (14.93 mL) in anhydrous THF (300 mL) under argon at −78° C. and the mixture is allowed to stir 20 minutes. A solution of 4-tert-butoxy-2,5,6-trifluoropyridine (15.58 g) in dry THF (30 mL) is added. Methyl iodide (9.45 mL) is added via syringe and the cooling bath is removed. After stirring 90 minutes, the slurry is poured into a saturated aqueous ammonium chloride solution (250 mL) and is extracted twice with hexanes. The combined organic layers are washed with water and brine and dried over MgSO4. Evaporation of the solvent provided the desired compound.

4-tert-Butoxy-2,5-difluoro-6-hydrazino-3-methylpyridine

Hydrazine monohydrate (16.6 mL) is added to a solution of 4-tert-butoxy-2,3,6-trifluoro-5-methylpyridine (13.19 g) in n-propanol (200 mL) and the resulting solution is refluxed under argon for 16 h. The mixture is cooled to room temperature and the solvent evaporated. The residue is redissolved in methylene chloride, washed with water, and dried over MgSO4. The desired product is obtained by evaporation of the solvent.

4-tert-Butoxy-2,5-difluoro-3-methylpyridine

Crude 4-tert-Butoxy-2,5-difluoro-6-hydrazino-3-methylpyridine (from the run above) is dissolved in methanol (150 mL) and a 20% aqueous sodium hydroxide solution (32 mL) is added. Air is bubbled through the reaction mixture as it stirred for 48 h. The solvent is removed and the residue is redissolved in methylene chloride. This organic layer is washed once with water and is dried over MgSO4 and the solvent evaporated. The desired product is purified by chromatography using hexanes/ether 95/5 as solvent.

2-(4-tert-Butoxy-5-fluoro-3-methyl-2-pyridinyl)cyclopropaneacetonitrile

Dry diisopropylamine (12.0 mL) is dissolved in anhydrous THF (80 mL). The solution is cooled to −78° C. and n-butyllithium (36.6 mL, 2.5 M in hexanes) is added. After 30 minutes, cyclopropylacetonitrile (3.6 g) is added in dry THF (20 mL). 4-tert-butoxy-2,5-difluoro-3-methyl-2-pyridine (7.37 g) in THF (20 mL) is then added. The mixture is allowed to stir 1 h at −78° C. and 1 hr at room temperature before it is poured into a saturated aqueous ammonium chloride solution (150 mL) and extracted twice with ether. The combined organic layers are washed with brine, dried over MgSO4, and concentrated to give a yellow oil. The oil is applied to a column of silica gel in 20% ethyl acetate in hexanes to give the desired product.

2-(4-Hydroxy-5-fluoro-3-methyl-2-pyridinyl)cyclopropaneacetonitrile 2-(4-tert-Butoxy-5-fluoro-3-methyl-2-pyridinyl)cyclopropaneacetonitrile (10.5 g) is dissolved in neat trifluoroacetic acid (100 mL) and stirred 1 h at room temperature. The trifluoroacetic acid is then removed to give the desired product.

2-(4-Chloro-5-fluoro-3-methyl-2-pyridinyl)cyclopropaneacetonitrile

Crude 2-(4-Hydroxy-5-fluoro-3-methyl-2-pyridinyl)cyclopropaneacetonitrile from the previous reaction is dissolved in dichloromethane (150 mL) and anhydrous N,N-dimethylformamide (30.9 mL) is added followed by phosphorous oxychloride (3.7 mL). This mixture is stirred for 48 hours at room temperature, then poured into cold water (150 mL) and extracted with dichloromethane. The pH of the aqueous layer is raised to 7 with 1 N NaOH. The aqueous layer is extracted twice more with dichloromethane and the combined organic layers are washed once with water, dried over MgSO$_4$, and concentrated. The desired product is purified by chromatography using hexanes/ethyl acetate 8/2 as solvent.

Ethyl 2-(4-chloro-5-fluoro-3-methyl-2-pyridinyl)cyclopropaneacetate

Hydrogen chloride gas is bubbled through a solution of 2-(4-chloro-5-fluoro-3-methyl-2-pyridinyl)cyclopropaneacetonitrile (2.91 g) in ethanol (9 mL) until the weight had increased by 3.56 g and heated to reflux. Water (0.32 mL) is added and the mixture is allowed to reflux 2 h before cooling to room temperature and adding water. The pH is adjusted to 7 with solid sodium bicarbonate and it is extracted with dichloromethane. The combined organic layers are washed with water, dried over MgSO$_4$, and concentrated to give a yellow liquid which is purified by column chromatography on silica gel in 20% ethyl acetate in hexanes to give the desired product.

2-(4-Chloro-5-fluoro-3-methyl-2-pyridinyl)cyclopropaneethanol

Ethyl 2-(4-chloro-5-fluoro-3-methyl-2-pyridinyl)cyclopropaneacetate (1.31 g) is dissolved in dry THF (10 mL). Lithium aluminum hydride (91.8 mg) is added to this solution and it is allowed to stir 1 h at room temperature. The reaction mixture is quenched with a saturated aqueous solution of sodium potassium tartrate (25 mL) and extracted with ether. The combined organic layers are dried with MgSO$_4$ and concentrated to give the desired product.

2-(4-Chloro-5-fluoro-3-methyl-2-pyridinyl)cyclopropaneacetaldehyde 2-(4-Chloro-5-fluoro-3-methyl-2-pyridinyl)cyclopropaneethanol is dissolved in dichloromethane (5 mL) and added to a solution of oxalyl chloride (0.51 mL) and dry DMSO (0.82 mL) in dichloromethane (12 mL) at −78° C. After stirring 15 minutes, triethylamine (3.31 mL) is added and the mixture stirred another 5 minutes at −78° C. and 10 minutes at 0° C. The reaction is then quenched with water and extracted with dichloromethane. The combined organic layers are washed with water, dried over MgSO$_4$, and concentrated to give the desired product.

Diethyl [(4-Chloro-5-fluoro-3-methyl-2-pyridinyl)cyclopropanemethylmethylene]-malonate Piperidine (1.14 mL), acetic acid (1.14 mL) and diethyl malonate (3.80 mL) are added to a solution of 2-(4-Chloro-5-fluoro-3-methyl-2-pyridinyl)cyclopropaneacetaldehyde in ethanol (40 mL) and the reaction mixture is heated at reflux under argon for 4 h. The solvents are removed and the residue is dissolved in ether. The ether layer is washed with water and brine, dried over MgSO$_4$ and concentrated. The desired product is purified by chromatography using hexane/ethyl acetate as solvent.

Ethyl 8-chloro-1-cycloprolyl-7-fluoro-9-methyl-4-oxo-4H-quinolizine-3-carboxylate A solution of Diethyl [(4-Chloro-5-fluoro-3-methyl-2-pyridinyl)cyclopropanemethyl-methylene]malonate (539.1 mg) in diphenyl ether (25 mL) is heated at 220° C. for 45 minutes, then allowed to cool to room temperature. The desired product is isolated by chromatography using hexane then ethyl acetate as solvent.

b. Precursor Preparation—7-Position Moiety:

Precursor Example F

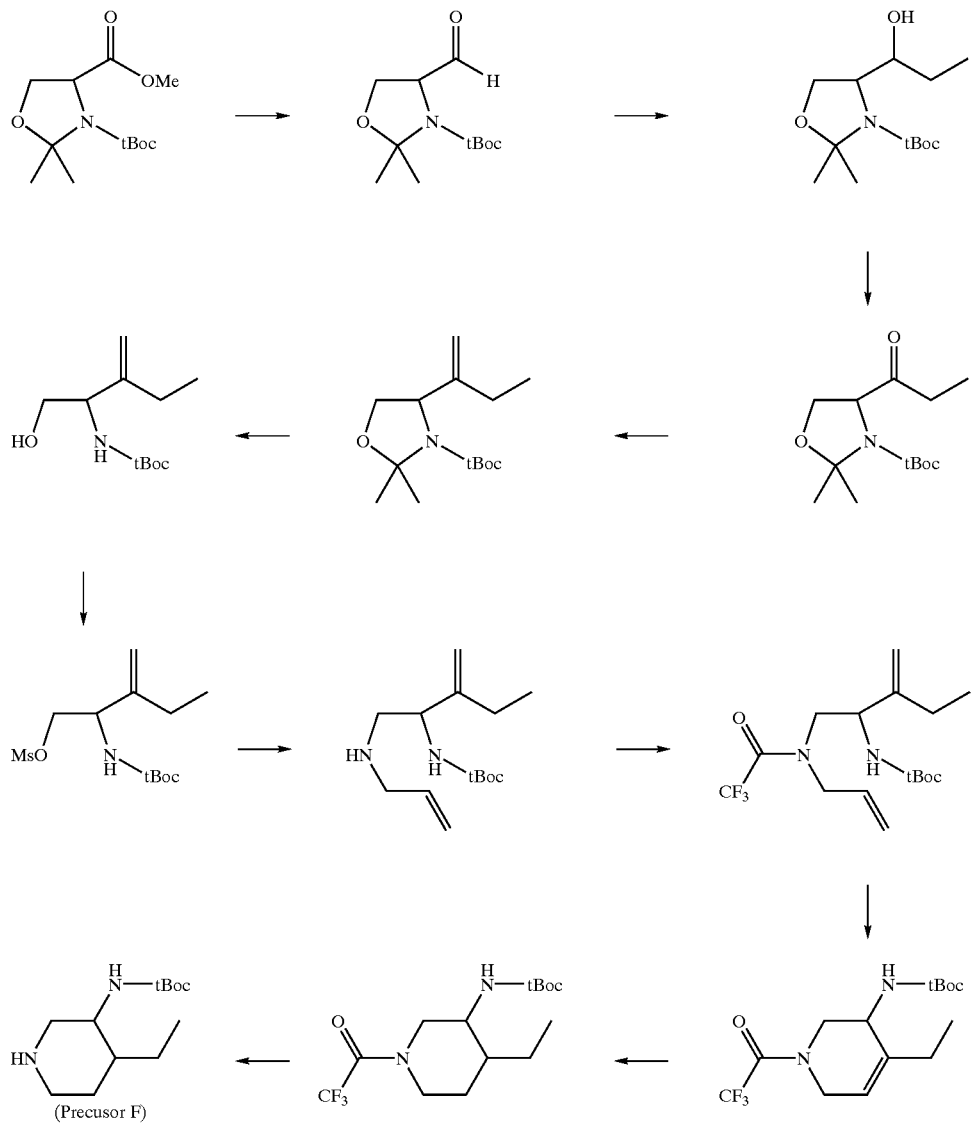

3-(tert-butoxycarbonyl)2,2-dimethyl-4-oxazolidinecarboxaldehyde

A solution of methyl 3-(tert-butoxycarbonyl)-2,2-dimethyl-4-oxazolidinecarboxylate (4.91 g) is dissolved in toluene (40 mL) and cooled to −78° C. To it a solution of diisobutylaluminum hydride ("DIBAL") (33.2 mL, 1 M) is added dropwise to maintain the internal temperature under −60° C. After the addition, the resulting solution is stirred at −78° C. for 30 min., and then slowly warmed to 0° C. in 2 hrs. The mixture is quenched by addition of water. The organic layer is separated and the aqueous layer is extracted once with ethyl acetate. The combined extracts are dried over anhydrous MgSO$_4$ and evaporated. The residue is purified by flash chromatography using ethyl acetate-hexanes.

3-(tert-butoxycarbonyl)2,2-dimethyl-4-(1-hydroxy-propyl)-oxazolidine

To a solution of 3-(tert-butoxycarbonyl)2,2-dimethyl-4-oxazolidinecarboxaldehyde (6.5 g) in THF (26 mL) is added a solution of EtMgBr (42.5 mL, 1 M in THF) dropwise at −78° C. After the addition, the resulting solution is allowed to warm to 0° C. in 1.5 hr and water is added to quench the reaction. The mixture is partitioned between sat. NaCl solution and ethyl acetate (EtOAc). The organic layer is separated and the aqueous layer is extracted with EtOAc twice. The combined extracts are dried over MgSO$_4$ and evaporated under reduced pressure. The crude product is purified by flash chromatography with EtOAc-Hexanes to give a colorless oil.

3-(tert-butoxycarbonyl)2,2-dimethyl-4-(1-oxo-propyl)-oxazolidine

A solution of oxalyl chloride (2.08 mL) in dichloromethane (70 mL) is cooled in an acetone-dry ice bath and to it is added dimethyl sulfide (3.53 mL) dropwise to control the internal temperature under −65° C. After stirring at that temperature for 5 min, a solution of 3-(tert-butoxycarbonyl) 2,2-dimethyl-4-(1-hydroxy-propyl)-oxazolidine (5.15 g) in dichloromethane is added in such a rate to control the internal temperature under −65° C. The resulting mixture is stirred at −78° C. for 30 min, and triethylamine (13.8 ml) is added in one portion. Stirring is continued for additional 5 min. The cold bath is removed and the reaction temperature is allowed to rise to room temperature in 30 min. Water is added to quench the reaction. The organic layer is separated and the aqueous layer is extracted with dichloromethane twice. The combined extracts are washed with brine and dried over MgSO$_4$ and evaporated under reduced pressure. The residue is purified by flash chromatography using EtOAc-Hexanes.

3-(tert-butoxycarbonyl)2,2-dimethyl-4-(1-buten-2yl)-oxazolidine

To a suspension of (CH$_3$)$_3$PPh$_3$Br (8.59 g) in anhydrous THF (40 mL) is added t-BuOK (2.7 g) in one portion at room temperature. After stirring for 10 min, the yellow mixture is treated with a solution of 3-(tert-butoxycarbonyl)2,2-dimethyl-4-(1-oxo-propyl)-oxazolidine (4.12 g) in THF. The mixture is stirred for an additional 10 min. and is then partitioned between sat. NaCl solution and EtOAc. The organic layer is separated and the aqueous layer is extracted with EtOAc twice. The combined extracts are dried over MgSO$_4$ and evaporated under reduced pressure. The residue is precipitated in ether and the formed white solid is removed by filtration. The filtrate is evaporated and the residue is purified by flash chromatography using EtOAc-Hexanes.

2-tert-butoxycarbonylamino-3-methylene-pentanol

A solution of 3-(tert-butoxycarbonyl)2,2-dimethyl-4-(1-buten-2yl)-oxazolidine (3.25 g) and p-TsOH.H$_2$O (0.484 g) in MeOH (100 mL) is heated at 50–60° C. for 18 hr. After cooling, the solvent is evaporated to ⅓ of its volume and diluted with EtOAc. The mixture is washed with sat. NaHCO$_3$ solution. The organic layer is separated and the aqueous is extracted with EtOAc two times. The combined extracts are dried over anhydrous MgSO$_4$ and evaporated. The residue is purified by flash chromatography with EtOAc-Hexanes.

2-tert-butoxycarbonylamino-3-methylene-1-methanesulfonylyloxy-pentane

A solution of 2-tert-butoxycarbonylamino-3-methylene-pentanol (1.37 g), methanesulfonyl chloride (0.592 g) and triehylamine (1.06 mL) in dichloromethane (20 ml) is stirred at 20° C. for 10 min., then is washed with a saturated solution of sodium bicarbonate followed by diluted HCl. The solvent is evaporated to afford the desired product.

2-tert-butoxycarbonylamino-3-methylene-N-(2-propenyl)-pentylamine

A solution of 2-tert-butoxycarbonylamino-3-methylene-1-methanesulfonylyloxy-pentane (1.87 g) and allylamine (4.77 mL) dissolved in dichloromethane is heated at reflux for 2 hrs. The solution is washed with sat. NaHCO$_3$. The organic layer is dried with anhydrous MgSO$_4$ and evaporated under reduced pressure to give the diene product

2-tert-butoxycarbonylamino-3-methylene-N-(2-propenyl)-N-trifluoroacteyl-pentylamine A solution of 2-tert-butoxycarbonylamino-3-methylene-N-(2-propenyl)-pentylamine (1.62 g), trifluoroacetic anhydride (0.82 mL) and Et$_3$N (0.89 mL) is stirred at <10° C. for 30 min. under argon. The mixture is washed with sat. NaHCO$_3$, dried over anhydrous MgSO$_4$ and evaporated. The residue is purified by flash chromatography using EtOAc-Hexanes.

1,2,3,6-tetrahydro-3-tert-butoxycarbonylamino-4-ethyl-1-trifluoroacetyl-pyridine 2-tert-butoxycarbonylamino-3-methylene-N-(2-propenyl)-N-trifluoroacteyl-pentylamine (1.05 g) and Grub's Ruthenium catalyst (0.247 g) are dissolved in dichloromethane (200 mL) and the solution is heated at reflux under argon for 20 hrs. The solvent is evaporated and the residue is purified by flash chromatography using EtOAc-Hexanes.

Trans 3-tert-butoxycarbonylamino-4-ethyl-1-trifluoroacetyl-piperidine

A mixture of 1,2,3,6-tetrahydro-3-tert-butoxycarbonylamino-4-ethyl-1-trifluoroacetyl-pyridine (0.865 g) and 10% Pd/C (0.086 g) in EtOH (35 mL) is subjected to the hydrogenation conditions at 1 atm H$_2$ pressure for 24 hr. The solid is removed by filtration and the filtrate is evaporated. The crude product is purified by flash chromatography using EtOAc-Hexanes.

Trans 3-tert-butoxycarbonylamino-4-ethyl-piperidine

A mixture of Trans 3-tert-butoxycarbonylamino-4-ethyl-1-trifluoroacetyl-piperidine (0.43 g) and K$_2$CO$_3$ (0.94 g) in MeOH (20 mL) and H$_2$O (5 mL) is heated at reflux for 30 min. The solid is removed by filtration and the filtrate is concentrated. The residue is partitioned between H$_2$O and dichloromethane. The organic layer is separated and the aqueous layer is extracted with dichloromethane. The combined extracts are dried over anhydrous MgSO$_4$ and evaporated.

Precursor Examples G and H
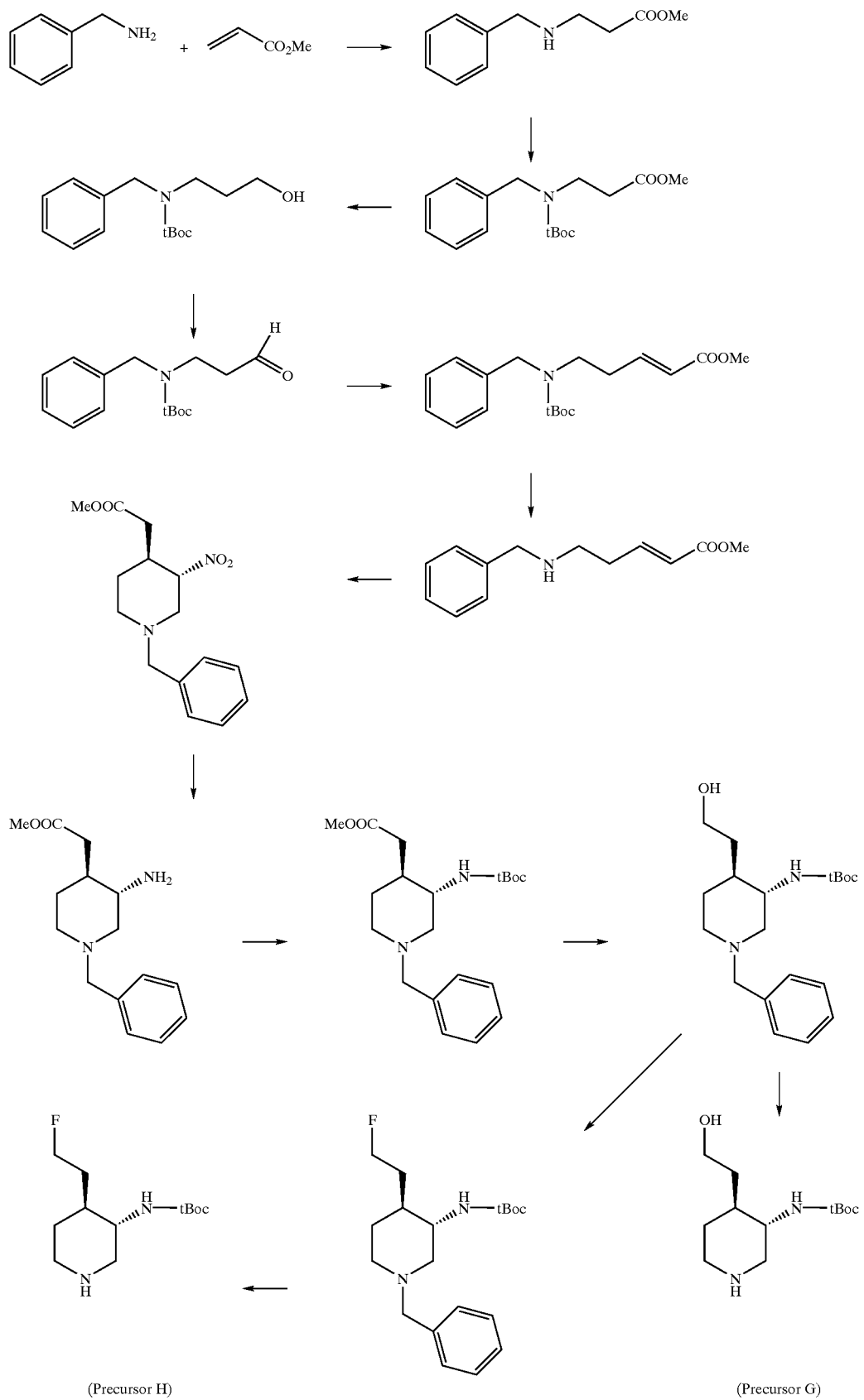
(Precursor H)
(Precursor G)

β3-alanine, N-benzyl-, methyl ester

Methyl acrylate (10 g) is dissolved in methanol (100 mL) and benzylamine (12.69 mL) is added. The solution is allowed to stir at room temperature for 24 hr. The reaction is concentrated and the residue is distilled (110–119° C. at 4 mbar) to give the desired product.

β-alanine, N-benzyl-N-tert-butoxycarbonyl, methyl ester

β-alanine, N-(benzyl)—, methyl ester (5 g), ditertbutyldicarbonate (5.65 g) and triethylamine (5.4 mL) are dissolved in dry methylene chloride and allowed to stir overnight. The reaction is washed with 3×water, dried over sodium sulfate, filtered and concentrated. The residue is purified by flash chromatography with 10% ethyl acetate/hexanes.

N-benzyl-3-tert-butoxycarbonylamino-1-propanol

β-alanine, N-benzyl-N-tert-butoxycarbonyl, methyl ester (8.3 g) is dissolved in toluene (125 mL) and cooled to −78° C. Dibal (85.2 mL, 1 M) solution in toluene is added slowly keeping temperature below −70° C. The reaction is then put in a constant temperature bath at −40° C. for 2 hr and then cooled back down to −70° C. The reaction is quenched with methanol (85 mL) and allowed to warm to room temperature. After 1 hr of stirring at room temperature the reaction is filtered through celite and the salts are washed with methanol. The combined filtrates are concentrated and the residue is dissolved in methylene chloride. The organic layer is washed with 2×1 N HCl and 1×brine. The organic layer is dried over sodium sulfate, filtered and concentrated. The residue is purified by flash chromatography with 12.5% ethyl acetate/hexanes.

N-benzyl-3-tert-butoxycarbonylamino-1-propanal

Oxalyl Chloride (2.07 mL) is dissolved in methylene chloride and cooled to −78° C. DMSO (3.2 mL) is added keeping the temperature below −60° C. The reaction is allowed to stir for 20 min. and then N-benzyl-3-tert-butoxycarbonylamino-1-propanol (3 g) in methylene chloride is added keeping the temperature below −60° C. The reaction is allowed to stir for 30 min., then triethylamine (13.2 mL) is added, allowed to warm to room temperature and stir for 1 hr. The reaction is diluted with methylene chloride and water. The layers are separated and the organic layer is washed twice with 1 N HCl and once with brine. The organic layer is dried over sodium sulfate, filtered and concentrated. The residue is purified by flash chromatography.

Methyl,N-benzyl-5-tert-butoxycarbonylamino-2-pentenoate

N-benzyl-3-tert-butoxycarbonylamino-1-propanal (1.46 g) is dissolved in toluene and methyl (triphenylphosphoranylidene)acetate (2.04 g) is added. The reaction is heated to reflux and allowed to stir overnight. After concentration, the residue is triturated with hexanes and filtered washing solids with hexanes. The filtrate is concentrated and the residue is purified by flash chromatography with 25% ethyl acetate/hexanes.

Methyl,N-benzyl-5-amino-2-pentenoate

Methyl,N-benzyl-5-tert-butoxycarbonylamino-2-pentenoate (1.68 g) is dissolved in methylene chloride and cooled to 0° C. Trifluoroacetic acid (4 mL) is added to make a 20% solution and is allowed to warm to room temp. The reaction is complete in 15 min. and diluted with methylene chloride. The reaction is washed with 3×sat. sodium bicarbonate and 1×brine. The methylene chloride is dried over sodium sulfate, filtered and concentrated to give the desired product.

Trans N-benzyl-4-(methylacetate-2-yl)-3-nitro-piperidine

Methyl,N-benzyl-5-amino-2-pentenoate (1.16 g) is dissolved in ethanol (12 mL) and 2-benzoyloxy-1-nitro-ethane (1.55 g) is added. The solution is allowed to stir at room temperature overnight and is then concentrated. The residue is dissolved in methylene chloride and washed 3 times with 100 mL sat. sodium bicarbonate and once with brine. The organic layer is dried over sodium sulfate, filtered and concentrated. The residue is purified by flash chromatography with 25% ethyl acetate/hexanes.

Trans N-benzyl-4-(methylacetate-2-yl)-3-amino-piperidine

Trans N-benzyl-4-(methylacetate-2-yl)-3-nitro-piperidine (0.67 G) is dissolved in THF (16 mL) and Raney nickel (100 mg) is added. The reaction is allowed to stir under hydrogen overnight. The reaction is not complete, so additional Raney nickel (100 mg) is added and allowed to stir under hydrogen for 8 hr. The reaction is filtered through Celite® and the filtrate is concentrated to give the desired product.

Trans N-benzyl-4-(methylacetate-2-yl)-3-tertbutoxycarbonylamino-piperidine

Trans N-benzyl-4-(methylacetate-2-yl)-3-amino-piperidine (0.863 g) and ditertbutyldicarbonate (0.72 g) are dissolved in methylene chloride. Triethylamine (0.68 mL) is added and allowed to stir overnight. The reaction is diluted with methylene chloride and washed with 2×water. The organic layer is dried over sodium sulfate filtered and concentrated. The residue is purified by flash chromatography with 25% ethyl acetate/hexanes.

Trans N-benzyl-4-(2-hydroxy-ethyl)-3-tertbutoxycarbonylamino-piperidine

Trans N-benzyl-4-(methylacetate-2-yl)-3-tertbutoxycarbonylamino-piperidine (0.45 g) is dissolved in THF (10 mL) and cooled to −78° C. A 1 M solution of lithium aluminum hydride in THF (7.44 mL) is added in four aliquots and allowed to stir for 45 min. between additions. The reaction is allowed to stir for 2 hr and is then quenched with water 15% NaOH (0.7 mL). The quenched reaction is filtered and the salts are washed with THF. The salts are suspended in THF and heated to reflux. The salts are filtered hot and washed with THF. The combined filtrates are concentrated and the residue is purified by flash chromatography with 3 to 5% methanol/methylene chloride.

Trans 4-(2-hydroxy-ethyl)-3-tertbutoxycarbonylamino-piperidine (Precursor G)

Trans N-benzyl-4(2-hydroxy-ethyl)-3-tertbutoxycarbonylamino-piperidine (0.19 g) is dissolved in methanol (2 mL) and acetic acid (1 drop). Palladium hydroxide (0.05 g) is added and allowed to stir overnight under hydrogen. The reaction is filtered through Celite® and the filtrate is concentrated to give the desired product, Precursor G.

Trans-N-benzyl-4-(2-fluoro-ethyl)-3-tertbutoxycarbonylamino-piperidine

Trans N-benzyl-4-(2-hydroxy-ethyl)-3-tertbutoxycarbonylamino-piperidine (0.21 g) is dissolved in dichloromethane and diethylaminosulfur trifluoride (0.5 mL) is added. The solution is allowed to stir at room temperature for 3 hr and is quenched with ethanol. After one hour at room temperature, the solution is washed with brine and the solvent evaporated. The desired product is obtained by flash chromatography with 3 to 5% methanol/methylene chloride.

Trans-4-(2-fluoro-ethyl)-3-tertbutoxycarbonylamino-piperidine (Precursor H)

Trans N-benzyl-4-(2-fluoro-ethyl)-3-tertbutoxycarbonyl-amino-piperidine (0.09 g) is dissolved in methanol (1 mL) and acetic acid (1 drop). Palladium hydroxide (0.025 g) is added and allowed to stir overnight under hydrogen. The reaction is filtered through Celite® and the filtrate is concentrated to give the desired product, Precursor H.

c. Final Product Preparation

EXAMPLE 1

7-(Trans-3-amino-4-ethyl-piperidine-1-yl)-1-Cyclopropyl-1,4-dihydro-6-fluoro-8-methoxy-4-oxo-quinoline-3-carboxylic Acid Hydrochloride

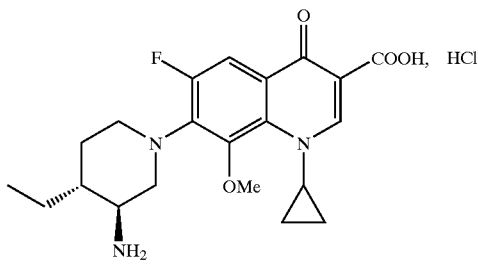

1-Cyclopropyl-1,4-dihydro-6,7-difluoro-8-methoxy-4-oxo-quinoline-3-carboxylic acid (Precursor A) (0.059 g), Trans,3-tert-butoxycarbonylamino-4-ethyl-piperidine (Precursor F) (0.048 mg) and triethylamine (0.075 mL) are dissolved in N-methyl-pyrrolidone (2 mL). The reaction mixture is stirred at 80° C. for 5 hours, then is poured on an ice/water mixture. The pH is lowered to 2 with diluted HCl and the resulting precipitate is filtered. The solid is then suspended in ethanol and 6N HCl is added. After 18 hours at room temperature, the desired final product is collected by filtration.

EXAMPLE 2

7-[Trans-3-amino-4-(2-hydroxy-ethyl)-piperidine-1-yl]-1-Cyclopropyl-1,4-dihydro-6-fluoro-8-methoxy-4-oxo-quinoline-3-carboxylic Acid Hydrochloride

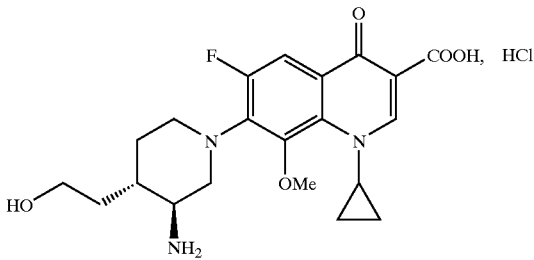

A procedure similar to Example 1 above is used, using 1-Cyclopropyl-1,4-dihydro-6,7-difluoro-8-methoxy-4-oxo-quinoline-3-carboxylic acid (Precursor A) and Trans 4-(2-hydroxy-ethyl)-3-tertbutoxycarbonylamino-piperidine (Precursor G) as the starting materials. The procedure utilizes the same reaction conditions and molar ratio of reactants as Example 1.

EXAMPLE 3

7-[Trans-3-amino-4-(2-fluoro-ethyl)-piperidine-1-yl]-1-Cyclopropyl-1,4-dihydro-6-fluoro-8-methoxy-4-oxo-quinoline-3-carboxylic Acid Hydrochloride

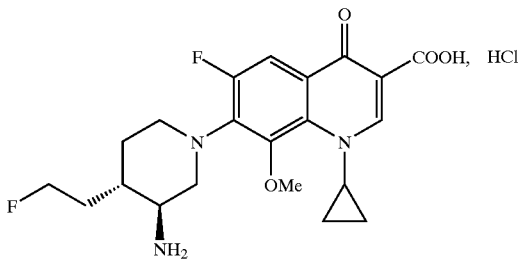

A procedure similar to Examples 1 and 2 above is used, but using as 1-Cyclopropyl-1,4-dihydro-6,7-difluoro-8-methoxy-4-oxo-quinoline-3-carboxylic acid (Precursor A) and Trans 4-(2-fluoro-ethyl)-3-tertbutoxycarbonylamino-piperidine (Precursor H) as the starting materials. The procedure utilizes the same reaction conditions and molar ratio of reactants as Examples 1 and 2.

EXAMPLE 4

7-(Trans-3-amino-4-ethyl-piperidine-1-yl)-1-Cyclopropyl-1,4-dihydro-6-fluoro-4-oxo-1,8-naphthyridine-3-carboxylic Acid Hydrochloride

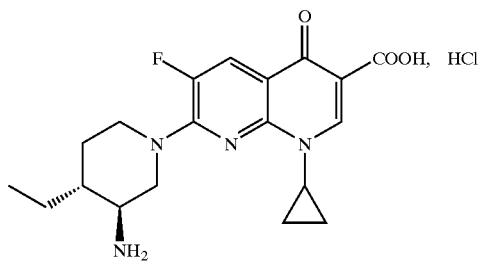

Ethyl-7-chloro-1-cyclopropyl-6-fluoro-4-oxo-1,4-dihydro-naphthyridine-3-carboxylate (Precursor B) (0.062 mg), trans,3-tert-butoxycarbonylamino-4-ethyl-piperidine (Precursor F) (48 mg) and triethylamine (0.05 mL) are dissolved in acetonitrile (1 mL) and stirred at room temperature for 18 hr. The solvent is evaporated under vacuum and the residue crystallized in water. The resulting solid is collected by filtration and suspended in a 1/1 mixture of 2N NaOH and ethanol (1 mL) and stirred at room temperature for 24 hours. The pH is then adjusted to 7.4 using 1N HCl and the precipitate is collected by filtration. The solid is resuspended in ethanol and treated with 6N hydrochloric acid for 18 hr at room temperature. The desired final product is collected by filtration.

EXAMPLE 5

7-[Trans-3-amino-4-(2-hydroxy-ethyl)-piperidine-1-yl]-1-Cyclopropyl-1,4-dihydro-6-fluoro-4-oxo-1,8-naphthyridine-3-carboxylic Acid Hydrochloride

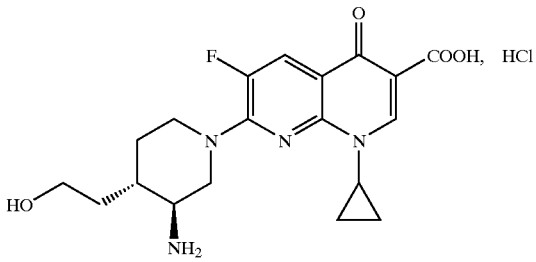

A procedure similar to Example 4 above is used using Ethyl-7-chloro-1-cyclopropyl-6-fluoro-4-oxo-1,4-dihydro-naphthyridine-3-carboxylate (Precursor B) and Trans 4-(2-hydroxy-ethyl)-3-tertbutoxycarbonylamino-piperidine (Precursor G) as the starting materials. The procedure utilizes the same reaction conditions and molar ratio of reactants as Example 4.

EXAMPLE 6

7-[Trans-3-amino-4-(2-fluoro-ethyl)-piperidine-1-yl]-1-Cyclopropyl-1,4-dihydro-6-fluoro-4-oxo-1,8-naphthyridine-3-carboxylic Acid Hydrochloride

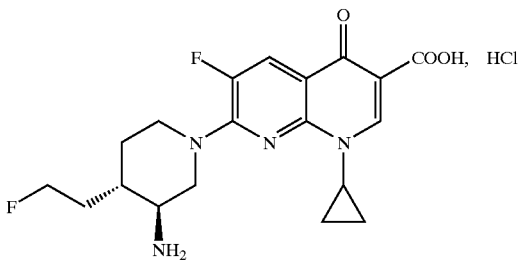

A procedure similar to Examples 4 and 5 above is used using Ethyl-7-chloro-1-cyclopropyl-6-fluoro-4-oxo-1,4-dihydro-naphthyridine-3-carboxylate (Precursor B) and Trans 4-(2-fluoro-ethyl)-3-tertbutoxycarbonylamino-piperidine (Precursor H) as the starting materials. The procedure utilizes the same reaction conditions and molar ratio of reactants as Examples 4 and 5.

EXAMPLE 7

(3S) 7-(Trans-3-amino-4-ethyl-piperidine-1-yl)-9-fluoro-2,3-dihydro-3-methyl-7-oxo-7H-pyrido[1,2,3-de]-1,4-benzoxazine-6-carboxylic Acid Hydrochloride

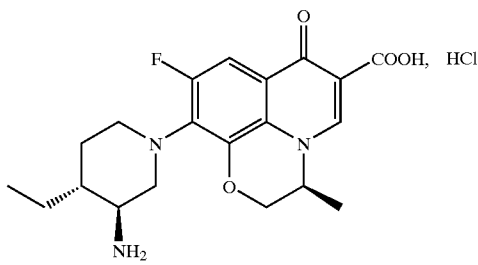

(3S) 9,10-difluoro-2,3-dihydro-3-methyl-7-oxo-7H-pyrido[1,2,3-de]-1,4-benzoxazine-6-carboxylic acid (Precursor C) (0.056 g), trans,3-tert-butoxycarbonylamino-4-ethyl-piperidine (Precursor F) (0.048 g) and triethylamine (0.075 mL) are dissolved in N-methyl-pyrrolidone (1 mL). The solution is stirred at 80° C. for 18 hr., then is poured on an ice/water mixture. The pH is lowered to 2 using diluted HCl and the resulting precipitate is collected by filtration. The solid is then suspended in ethanol and 6N HCl is added. After 18 hr at room temperature, the desired product is collected by filtration.

EXAMPLE 8

(3S) 7-[Trans-3-amino-4-(2-hydroxyethyl)-piperidine-1-yl]-9-fluoro-2,3-dihydro-3-methyl-7-oxo-7H-pyrido[1,2,3-de]-1,4-benzoxazine-6-carboxylic Acid Hydrochloride

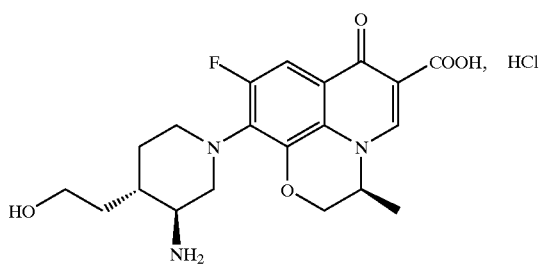

A procedure similar to Example 7 above is used using 9,10-difluoro-2,3-dihydro-3-methyl-7-oxo-7H-pyrido[1,2,3-de]-1,4-benzoxazine-6-carboxylic acid (Precursor C) and Trans 4-(2-hydroxy-ethyl)-3-tertbutoxycarbonylamino-piperidine (Precursor G) as the starting materials. The procedure utilizes the same reaction conditions and molar ratio of reactants as Example 7.

EXAMPLE 9

(3S) 7-[Trans-3-amino-4-(2-fluoroethyl)-piperidine-1-yl]-9-fluoro-2,3-dihydro-3-methyl-oxo-7H-pyrido[1,2,3-de]-1,4-benzoxazine-6-carboxylic Acid Hydrochloride

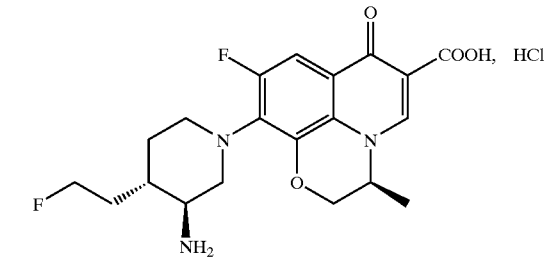

A procedure similar to Examples 8 and 9 above is used using 9,10-difluoro-2,3-dihydro-3-methyl-7-oxo-7H-pyrido[1,2,3-de]-1,4-benzoxazine-6-carboxylic acid (Precursor C) and Trans 4-(2-fluoro-ethyl)-3-tertbutoxycarbonylamino-piperidine (Precursor H) as the starting materials. The procedure utilizes the same reaction conditions and molar ratio of reactants as Examples 7 and 8.

EXAMPLE 10

(3S) 7-(Trans-3-amino-4-ethyl-piperidine-1-yl)-5,6,8-trifluoro-9-cyclopropyl-1,3,4,9-tetrahydroisothiazolo[5,4-b]quinoline-3,4-dione

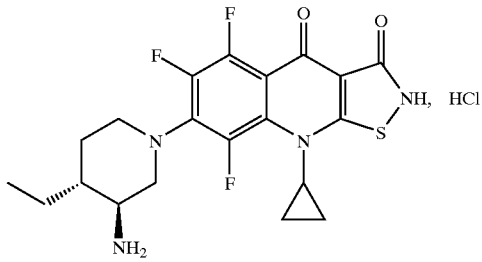

5,6,7,8-tetrafluoro-9-cyclopropyl-1,3,4,9-tetrahydroisothiazolo[5,4-b]quinoline-3,4-dione (Precursor D) (0.067 g) is suspended in dimethylformamide (DMF) (1 mL) and trans,3-tert-butoxycarbonylamino-4-ethyl-piperidine (Precursor F) (0.048 g) and then triethylamine (0.05 mL) are added. The reaction is stirred at 50° C. for 6 hr. The mixture is concentrated under vacuum, and the residue is triturated in water. The precipitate is collected in water, rinsed with ethanol and suspended in ethanol. Drops of 12N HCl are added and the suspension is stirred for 12 hr at 20° C. The desired product is collected by filtration.

EXAMPLE 11

(3S) 7-[Trans-3-amino-4-(2-hydroxyethyl)-piperidine-1-yl]-5,6,8-trifluoro-9-cyclopropyl-1,3,4,9-tetrahydroisothiazolo[5,4-b]quinoline-3,4-dione

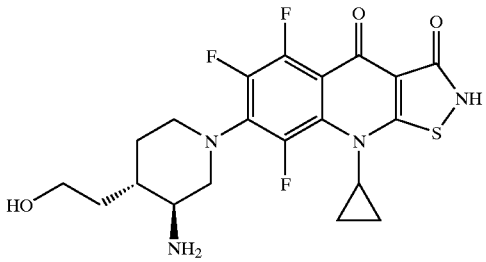

A procedure similar to Example 10 above is used using 5,6,7,8-tetrafluoro-9-cyclopropyl-1,3,4,9-tetrahydroisothiazolo[5,4-b]quinoline-3,4-dione (Precursor D) and Trans 4-(2-hydroxy-ethyl)-3-tertbutoxycarbonylamino-piperidine (Precursor G) as the starting materials. The procedure utilizes the same reaction conditions and molar ratio of reactants as Example 10.

EXAMPLE 12

(3S) 7-[Trans-3-amino-4-(2-fluoroethyl)-piperidine-1-yl]-5,6,8-trifluoro-9-cyclopropyl-1,3,4,9-tetrahydroisothiazolo[5,4-b]quinoline-3,4-dione

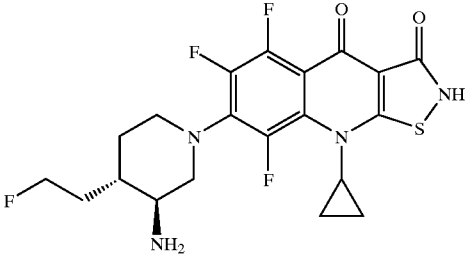

A procedure similar to Examples 10 and 11 above is used using 5,6,7,8-tetrafluoro-9-cyclopropyl-1,3,4,9-tetrahydroisothiazolo[5,4-b]quinoline-3,4-dione (Precursor D) and Trans 4-(2-fluoro-ethyl)-3-tertbutoxycarbonyl-amino-piperidine (Precursor H) as the starting materials. The procedure utilizes the same reaction conditions and molar ratio of reactants as Examples 10 and 11.

EXAMPLE 13

8-[(3S)-trans-3-amino-4-ethyl-piperidine-1-yl]-1-cyclopropyl-7-fluoro-9-methyl-4-oxo-4H-quinolizine-3-carboxylic acid dihydrochloride

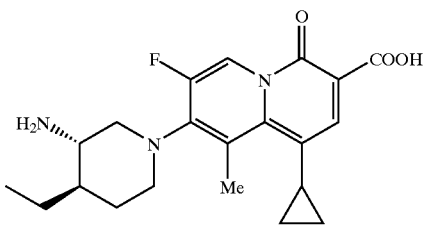

Ethyl 8-[(3S)-trans-3-amino-4-ethyl-piperidine-1-yl]-1-cyclopropyl-7-fluoro-9-methyl-4-oxo-4H-quinolizine-3-carboxylate A solution of Ethyl 8-chloro-1-cyclopropyl-7-fluoro-9-methyl-4-oxo-4H-quinolizine-3-carboxylate (precursor E) (40 mg), trans 3-tert-butoxycarbonylamino-4-ethyl-piperidine (precursor F) (0.124 mmol) and Et$_3$N (0.034 mL) in DMF (2 mL) is stirred at room temperature for 3 days. The solvent is evaporated under reduced pressure. The residue is dissolved in CH$_2$Cl$_2$, washed with 0.1 M HCl solution, dried over anhydrous MgSO$_4$ and evaporated to give desired product.

8-[(3S)-trans-3-t-butoxycarbonylamino-4-ethyl-piperidine-1-yl]-1-cyclopropyl-7-fluoro-9-methyl-4-oxo-4H-quinolizine-3-carboxylic Acid A solution of Ethyl 8-[(3S)-trans-3-t-butoxycarbonylamino-4-ethyl-piperidine-1-yl]-1-cyclopropyl-7-fluoro-9-methyl-4-oxo-4H-quinolizine-3-carboxylate (62 mg) and 16% NaOH (0.15) in EtOH (2 mL) is stirred at room temperature for 6 hr. The mixture is partitioned between CH$_2$Cl$_2$ and 0.1 N HCl solution. The organic layer is separated and the aqueous Layer is extracted with CH$_2$Cl$_2$ twice. The combined extracts are dried over anhydrous MgSO4 and evaporated to afford 60 mg of a yellow solid. The crude product (40 mg) is purified by preparative HPLC using a CH$_3$CN—H$_2$O-TFA system to elute the column and the product is obtained by concentration of the fraction.

8-[(3S)-trans-3-amino-4-ethyl-piperidine-1-yl]-1-cyclopropyl-7-fluoro-9-methyl-4-oxo-4H-quinolizine-3-carboxylic Acid Dihydrochloride 8-[(3S)-trans-3-t-butoxycarbonylamino-4-ethyl-piperidine-1-yl]-1-cyclopropyl-7-fluoro-9-methyl-4-oxo-4H-quinolizine-3-carboxylic acid (27 mg, 0.055 mmol) is treated with conc. HCl (0.5 mL) for 10 min. The volatiles are evaporated under reduced pressure to afford the title compound.

EXAMPLE 14

8-[(3S)-trans-3-amino-4-(2-hydroxy-ethyl)-piperidine-1-yl]-1-cyclopropyl-7-fluoro-9-methyl-4-oxo-4H-quinolizine-3-carboxylic Acid Dihydrochloride

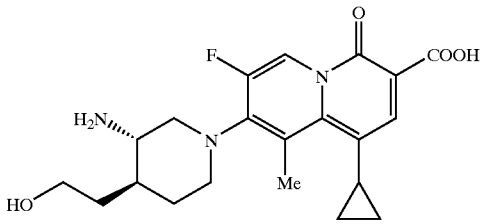

A procedure similar to Example 13 above is used, using Ethyl 8-chloro-1-cyclopropyl-7-fluoro-9-methyl-4-oxo-4H-quinolizine-3-carboxylate (Precursor E) and Trans 4-(2-hydroxy-ethyl)-3-tertbutoxycarbonylamino-piperidine (Precursor G) as the starting materials. The procedure utilizes the same reaction conditions and molar ratio of reactants as Example 13.

EXAMPLE 15

8-[(3S)-trans-3-amino-4-(2-fluoro-ethyl)-piperidine-1-yl]-1-cyclopropyl-7-fluoro-9-methyl-oxo-4H-quinolizine-3-carboxylic Acid Dihydrochloride

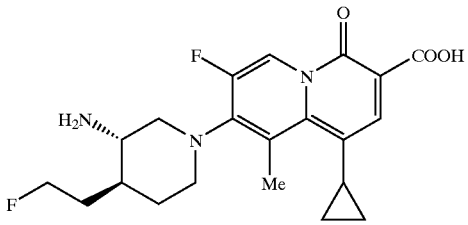

A procedure similar to Example 13 above is used, using Ethyl 8-chloro-1-cyclopropyl-7-fluoro-9-methyl-4-oxo-4H-quinolizine-3-carboxylate (Precursor E) and Trans 4-(2-fluoro-ethyl)-3-tertbutoxycarbonylamino-piperidine (Precursor H) as the starting materials. The procedure utilizes the same reaction conditions and molar ratio of reactants as Example 13.

VII. Examples—Compositions and Methods of Use

The following non-limiting examples illustrate the compositions and methods of use of the present invention.

EXAMPLE 16

A tablet composition for oral administration, according to the present invention, is made comprising:

| Component | Amount |
| --- | --- |
| Compound of Example 1 | 150 mg |
| Lactose | 120 mg |
| Maize Starch | 70 mg |
| Talc | 4 mg |
| Magnesium Stearate | 1 mg |

Other compounds having a structure according to Formula (I) are used with substantially similar results.

EXAMPLE 17

A capsule containing 200 mg of active for oral administration, according to the present invention, is made comprising:

| Component | Amount (% w/w) |
| --- | --- |
| Compound of Example 4 | 15% |
| Hydrous Lactose | 43% |
| Microcrystalline Cellulose | 33% |
| Crosspovidone | 3.3% |
| Magnesium Stearate | 5.7% |

Other compounds having a structure according to Formula (I) are used with substantially similar results.

EXAMPLE 18

A saline-based composition for ocular administration, according to the present invention, is made comprising:

| Component | Amount (% w/w) |
| --- | --- |
| Compound of Example 7 | 10% |
| Saline | 90% |

Other compounds having a structure according to Formula (I) are used with substantially similar results.

EXAMPLE 19

An intranasal composition for local administration, according to the present invention, is made comprising:

| Component | Composition (% w/w) |
| --- | --- |
| Compound of Example 10 | 0.20 |
| Benzalkonium chloride | 0.02 |
| EDTA | 0.05 |
| Glycerin | 2.0 |
| PEG 1450 | 2.0 |
| Aromatics | 0.075 |
| Purified water | q.s. |

Other compounds having a structure according to Formula (I) are used with substantially similar results.

EXAMPLE 20

An inhalation aerosol composition, according to the present invention, is made comprising:

| Component | Composition (% w/w) |
|---|---|
| Compound of Example 14 | 5.0 |
| Ascorbic acid | 0.1 |
| Menthol | 0.1 |
| Sodium Saccharin | 0.2 |
| Propellant (F12, F114) | q.s. |

Other compounds having a structure according to Formula (I) are used with substantially similar results.

EXAMPLE 21

A topical opthalmic composition, according to the present invention, is made comprising:

| Component | Composition (% w/w) |
|---|---|
| Compound of Example 15 | 0.10 |
| Benzalkonium chloride | 0.01 |
| EDTA | 0.05 |
| Hydroxyethylcellulose | 0.5 |
| Acetic acid | 0.20 |
| Sodium metabisulfite | 0.10 |
| Sodium chloride (0.9%) | q.s. |

Other compounds having a structure according to Formula (I) are used with substantially similar results.

EXAMPLE 22

An antimicrobial composition for parenteral administration, according to this invention, is made comprising:

| Component | Amount |
|---|---|
| Compound of Example 12 | 30 mg/mL excipient |
| Excipient: | |
| 50 mm phosphate buffer pH 5 buffer with lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated. Other compounds having a structure according to Formula (1) are used with substantially similar results.

EXAMPLE 23

An enteric coated antimicrobial composition for oral administration, according to this invention, is made comprising the following core tablet:

| Component | Amount (mg) |
|---|---|
| Compound of Example 5 | 350.0 |
| Maltodextrine | 30.0 |
| Magnesium Stearate | 5.0 |
| Microcrystalline Cellulose | 100.0 |
| Colloidal Silicon Dioxide | 2.5 |
| Povidone | 12.5 |

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 4 days. Symptoms of the disease then subside, indicating substantial eradication of the pathogen. Other compounds having a structure according to Formula (I) are used with substantially similar results.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

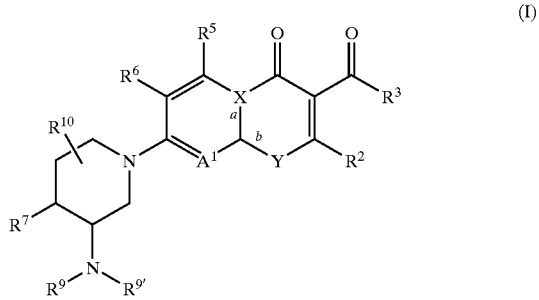

wherein:

(A)

(1) $A^1$ —is $C(R^8)$—, where $R^8$ is selected from hydrogen, halo, $C_1$ to about $C_6$ alkoxy, $C_1$ to about $C_6$ alkylthio, $C_1$ to about $C_6$ alkyl, $C_2$ to about $C_6$ alkene and alkyne;

(2)

(a) X is —C—, a is a double bond and b is a single bond; and (b) Y is —N($R^1$)—;

(3) $R^1$ is selected from $C_3$ to about $C_6$ cycloalkyl, $C_4$ to about $C_6$ heterocycloalkyl, $C_1$ to about $C_6$ alkyl, $C_2$ to about $C_6$ alkene, a 6-membered aryl and a 6-membered heteroaryl;

(4) $R^2$ is hydrogen;

(5) R³ is selected from hydrogen and hydroxy;
(6) R⁵ is selected from hydrogen, hydroxy, amino, halo, $C_1$ to about $C_6$ alkyl, $C_2$ to about $C_6$ alkene- and $C_1$ to about $C_6$ alkoxy;
(7) R⁶ is selected from fluoro and chloro;
(8) R⁷ is —Q—C(R¹¹)(R¹¹')(R¹¹"), where Q is selected from —S—, —O— and —C(R¹²)(R¹²')—, where R¹² and R¹²' are each independently selected from hydrogen and fluoro; where R¹¹, R¹¹' and R¹¹" are each independently selected from hydrogen, hydroxy and halo; and where R¹¹ and R¹² may also both be nil, such that a double bond is formed between the respective carbon atoms;
(9) R⁹ and R⁹' are each independently selected from hydrogen and $C_1$ to about $C_{15}$ alkyl, or R⁹ and R⁹' join to form a heterocyclic ring containing the nitrogen atom to which they are bonded; and
(10) R¹⁰ represents the moieties on the piperidine ring other than R⁷ and —NR⁹R⁹', where each R¹⁰ is independently selected from hydrogen, $C_1$ to about $C_6$ alkyl and fluoro;
or an optical isomer, diastereomer or enantiomer thereof; a pharmaceutically-acceptable salt, hydrate, or biohydrolyzable ester, amide or imide thereof.

2. A compound of claim 1 wherein R¹ is selected from $C_3$ to about $C_6$ cycloalkyl, $C_3$ to about $C_6$ heterocycloalkyl, $C_1$ to about $C_4$ alkyl and $C_2$ to about $C_4$ alkene.

3. A compound of claim 2 wherein R¹ is selected from cyclopropyl, methyl, ethyl, t-butyl, 4-hydroxyphenyl and 2,4-difluorophenyl.

4. A compound of claim 1 wherein R³ is hydroxy.

5. A compound of claim 1 wherein R⁵ is selected from hydrogen, hydroxy, chloro, bromo, amino, methyl, monofluoromethyl, difluoromethyl and trifluoromethyl.

6. A compound of claim 1 wherein each of R¹¹, R¹¹' and R¹¹" is hydrogen.

7. A compound of claim 1 wherein R⁷ is selected from methoxy, thiomethoxy and ethyl.

8. A compound of claim 7 wherein R⁷ is ethyl.

9. A compound of claim 1 wherein R⁹ and R⁹' are each independently selected from hydrogen and methyl.

10. A compound of claim 9 wherein R⁹ and R⁹' are both hydrogen and each R¹⁰ is hydrogen.

11. A compound having a structure according to Formula (II)

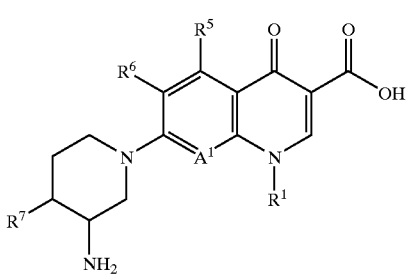

wherein:
(A)
(1) A¹ is —C(R⁸)— where R⁸ is selected from hydrogen, halo, $C_1$ to about $C_6$ alkoxy, $C_1$ to about $C_6$ alkylthio, $C_1$ to about $C_6$ alkyl, $C_2$ to about $C_6$ alkene and $C_2$ to about $C_6$ alkyne;
(2) R¹ is selected from $C_3$ to about $C_6$ cycloalkyl, $C_4$ to about $C_6$ heterocycloalkyl, $C_1$ to about $C_6$ alkyl, $C_1$ to about $C_6$ alkene, a 6-membered aryl and a 6-membered heteroaryl;
(5) R⁵ is selected from hydrogen, hydroxy, amino, halo, $C_1$ to about $C_6$ alkyl, $C_1$ to about $C_6$ alkene- and $C_1$ to about $C_6$ alkoxy;
(6) R⁶ is selected from fluoro and chloro; and
(7) R⁷ is —QC(R¹¹)(R¹¹')(R¹"), where Q is selected from —S—, —O— and —C(R¹²)(R¹²')—, where R¹² and R¹²' are each independently selected from hydrogen and fluoro; where R¹¹, R¹¹' and R¹¹" are each independently selected from hydrogen, hydroxy and halo; and where R¹¹ and R¹² may also both be nil, such that a double bond is formed between the respective carbon atoms;

or an optical isomer, diastereomer or enantiomer thereof, or a pharmaceutically-acceptable salt, hydrate, or biohydrolyzable ester, amide or imide thereof.

12. A compound of claim 11 wherein R⁶ is fluoro.

13. A compound of claim 11 wherein R¹ is selected from cyclopropyl, methyl, ethyl, t-butyl, 4-hydroxyphenyl and 2,4-difluorophenyl.

14. A compound of claim 12 wherein R⁵ is selected from hydrogen, hydroxy, chloro, bromo, amino, methyl, monofluoromethyl, difluoromethyl and trifluoromethyl.

15. A compound of claim 12 wherein R⁷ is selected from methoxy, thiomethoxy and ethyl.

16. A compound of claim 15 wherein R⁷ is ethyl.

17. A pharmaceutical composition comprising:

(a) a safe and effective amount of a compound of claim 1; and (b) a pharmaceutically-acceptable excipient.

18. A pharmaceutical composition comprising:

(a) a safe and effective amount of a compound of claim 11; and (b) a pharmaceutically-acceptable excipient.

19. A method for treating microbial infection comprising administering to a host in need of such a treatment a safe and antimicrobially effective amount of a compound of claim 1.

20. A method for treating microbial infection comprising administering to a host in need of such a treatment a safe and antimicrobially effective amount of a compound of claim 11.

* * * * *

UNITED STATES PATENT AND TRADEMARK OFFICE
CERTIFICATE OF CORRECTION

PATENT NO.     : 6,645,981 B2
DATED          : November 11, 2003
INVENTOR(S)    : Benoit Ledoussal et al.

It is certified that error appears in the above-identified patent and that said Letters Patent is hereby corrected as shown below:

Title page,
Item [74], *Attorney, Agent, or Firm*, delete "David V. Upita" and insert
-- David V. Upite --.

Column 1,
Line 47, insert a period -- . -- after the word "considerations", insert missing portion of new paragraph before "there is a ...":
    -- However, many such attempts to produce improved antimicrobials yield equivocal results. Indeed, few antimicrobials are prduced that are truly clinically-acceptable in thers of their spectrum of antimicrobial activity, avoidance of microbial resistance, and pharmacology. Thus --.

Column 32,
Line 15, delete "R" and insert -- $R^7$ --.

Column 38,
Line 34, delete "bums" and insert -- burns --.

Column 46,
Lines 40, 53 and 64, delete "MgSO4" and insert -- $MgSO_4$ --.

Column 49,
Lines 41 and 52, delete "MgSO4" and insert -- $MgSO_4$ --.

Column 50,
Line 1, delete "MgSO4" and insert -- $MgSO_4$ --.

UNITED STATES PATENT AND TRADEMARK OFFICE
CERTIFICATE OF CORRECTION

PATENT NO. : 6,645,981 B2
DATED : November 11, 2003
INVENTOR(S) : Benoit Ledoussal et al.

It is certified that error appears in the above-identified patent and that said Letters Patent is hereby corrected as shown below:

Column 70,
Lines 11 and 14, delete "$C_1$" and insert -- $C_2$ --.
Line 17, delete "-QC" and insert -- -Q-C --.

Signed and Sealed this

Fourteenth Day of March, 2006

JON W. DUDAS
*Director of the United States Patent and Trademark Office*